US008685675B2

(12) United States Patent
Millar

(10) Patent No.: US 8,685,675 B2
(45) Date of Patent: Apr. 1, 2014

(54) ENZYMES FOR AMPLIFICATION AND COPYING BISULPHITE MODIFIED NUCLEIC ACIDS

(75) Inventor: Douglas Spencer Millar, Revesby (AU)

(73) Assignee: Human Genetic Signatures Pty. Ltd., North Ryde, NSW (AU)

( * ) Notice: Subject to any disclaimer, the term of this patent is extended or adjusted under 35 U.S.C. 154(b) by 372 days.

(21) Appl. No.: 12/744,305

(22) PCT Filed: Nov. 27, 2008

(86) PCT No.: PCT/AU2008/001751
§ 371 (c)(1),
(2), (4) Date: Jul. 30, 2010

(87) PCT Pub. No.: WO2009/067743
PCT Pub. Date: Jun. 4, 2009

(65) Prior Publication Data
US 2010/0304386 A1    Dec. 2, 2010

(30) Foreign Application Priority Data

Nov. 27, 2007   (AU) ................................ 2007906490

(51) Int. Cl.
*C12P 19/34*   (2006.01)
*C12Q 1/68*    (2006.01)
(52) U.S. Cl.
USPC ........................................................ 435/91.2
(58) Field of Classification Search
None
See application file for complete search history.

(56) References Cited

U.S. PATENT DOCUMENTS

| | | | |
|---|---|---|---|
| 5,124,327 A * | 6/1992 | Greenlee et al. ............ 514/235.2 |
| 5,175,273 A | 12/1992 | Bischofberger et al. |
| 5,414,077 A | 5/1995 | Lin et al. |
| 5,418,149 A | 5/1995 | Gelfand et al. |
| 5,629,156 A | 5/1997 | Shah et al. |
| 5,656,744 A | 8/1997 | Arnold et al. |
| 5,750,338 A | 5/1998 | Collins et al. |
| 5,786,146 A | 7/1998 | Herman et al. |
| 5,824,517 A | 10/1998 | Cleuziat et al. |
| 5,952,174 A | 9/1999 | Nikiforov et al. |
| 6,156,501 A | 12/2000 | McGall et al. |
| 6,251,637 B1 | 6/2001 | Blusch |
| 6,265,171 B1 | 7/2001 | Herman et al. |
| 6,331,393 B1 | 12/2001 | Laird et al. |
| 6,420,106 B1 | 7/2002 | Gyllensten et al. |
| 6,521,411 B2 | 2/2003 | Hecker et al. |
| 6,692,918 B2 | 2/2004 | Kurn |
| 6,960,436 B2 | 11/2005 | Cottrell |
| 7,008,770 B1 | 3/2006 | Berlin |
| 7,288,373 B2 | 10/2007 | Millar et al. |
| 7,413,855 B2 | 8/2008 | Bergmann et al. |
| 7,504,207 B2 | 3/2009 | Bergquist |
| 7,527,948 B2 | 5/2009 | Hudson et al. |
| 7,799,525 B2 | 9/2010 | Millar |
| 7,803,580 B2 | 9/2010 | Millar |
| 7,833,942 B2 | 11/2010 | Millar et al. |
| 7,846,693 B2 | 12/2010 | Millar et al. |
| 8,168,777 B2 | 5/2012 | Millar et al. |
| 2002/0086324 A1 | 7/2002 | Laird et al. |
| 2002/0142397 A1 | 10/2002 | Collas et al. |
| 2003/0073081 A1 | 4/2003 | Mukai et al. |
| 2003/0082600 A1 | 5/2003 | Olek et al. |
| 2003/0119025 A1 | 6/2003 | Olek et al. |
| 2003/0143577 A1 | 7/2003 | Hogrefe et al. |
| 2004/0067559 A1 | 4/2004 | McCarthy et al. |
| 2004/0086944 A1 | 5/2004 | Grigg et al. |
| 2004/0203004 A1 | 10/2004 | Bernard et al. |
| 2004/0219539 A1 | 11/2004 | Millar et al. |
| 2005/0019762 A1 | 1/2005 | Olek |
| 2005/0059003 A1 | 3/2005 | Enoki et al. |
| 2005/0118578 A1 | 6/2005 | Mineno et al. |
| 2005/0136417 A1 | 6/2005 | Cole et al. |
| 2005/0196392 A1 | 9/2005 | Andersen |
| 2005/0196792 A1 | 9/2005 | Fodor et al. |
| 2005/0202490 A1 | 9/2005 | Makarov |
| 2006/0014144 A1 | 1/2006 | Christensen et al. |
| 2006/0051771 A1 | 3/2006 | Murphy et al. |
| 2006/0068406 A1 | 3/2006 | Affholter et al. |
| 2006/0094009 A1 | 5/2006 | Vaughan et al. |
| 2006/0166203 A1 | 7/2006 | Tooke |
| 2006/0286576 A1 | 12/2006 | Lofton-Day |
| 2007/0020633 A1 | 1/2007 | Millar |
| 2007/0020639 A1 | 1/2007 | Shapero |
| 2007/0020653 A1 | 1/2007 | Holliger |
| 2007/0026070 A1 | 2/2007 | Vonwiller |
| 2007/0042365 A1 | 2/2007 | Millar et al. |

(Continued)

FOREIGN PATENT DOCUMENTS

| | | | |
|---|---|---|---|
| AU | WO2004/096825 | * 11/2004 | ............. C12P 19/34 |
| DE | 103 31 107 B3 | 12/2004 | |
| EP | 1 130 113 | 9/2001 | |
| EP | 1 319 718 | 6/2003 | |
| EP | 1 443 052 | 8/2004 | |
| EP | 1 801 213 A2 | 6/2007 | |
| EP | 180123 | * 6/2007 | ............. C12N 9/12 |
| WO | WO 95/01456 | 1/1995 | |
| WO | WO 95/22623 | 8/1995 | |
| WO | WO 97/41254 | 11/1997 | |

(Continued)

OTHER PUBLICATIONS

Raizis et at (Analytical Biochem, 1995, vol. 226, p. 161-166, IDS reference).*
Bessho et al. (Nucleic Acids Research, 1992, vol. 20, No. 16, p. 4213-4220).*

(Continued)

*Primary Examiner* — Stephanie K Mummert
(74) *Attorney, Agent, or Firm* — Knobbe Martens Olson & Bear LLP

(57) ABSTRACT

The invention relates to the use of enzymes for copying or amplifying bisulphite modified or treated nucleic acids, wherein the enzymes are more effective in copying or amplifying the nucleic acid compared with native Taq polymerase under substantially the same conditions.

11 Claims, 3 Drawing Sheets

(56) References Cited

U.S. PATENT DOCUMENTS

| | | |
|---|---|---|
| 2007/0065824 A1 | 3/2007 | Gutig |
| 2007/0178457 A1 | 8/2007 | Millar |
| 2007/0178459 A1 | 8/2007 | Millar |
| 2007/0190530 A1 | 8/2007 | Birkner et al. |
| 2007/0264653 A1 | 11/2007 | Berlin et al. |
| 2008/0050738 A1 | 2/2008 | Millar |
| 2009/0029346 A1 | 1/2009 | Millar et al. |
| 2009/0042732 A1 | 2/2009 | Millar |
| 2009/0130657 A1 | 5/2009 | Millar |
| 2009/0263909 A1 | 10/2009 | Millar |
| 2010/0041013 A1 | 2/2010 | Millar et al. |
| 2010/0092972 A1 | 4/2010 | Millar et al. |
| 2010/0121056 A1 | 5/2010 | Christensen et al. |
| 2010/0221785 A1 | 9/2010 | Millar et al. |
| 2010/0286379 A1 | 11/2010 | Millar et al. |
| 2010/0304386 A1 | 12/2010 | Millar |
| 2011/0003700 A1 | 1/2011 | Millar |
| 2011/0136098 A1 | 6/2011 | Millar et al. |
| 2012/0021461 A1 | 1/2012 | Millar et al. |

FOREIGN PATENT DOCUMENTS

| | | |
|---|---|---|
| WO | WO 97/45559 | 12/1997 |
| WO | WO 98/20157 | 5/1998 |
| WO | WO 98/29108 | 7/1998 |
| WO | WO 99/09211 A2 | 2/1999 |
| WO | WO 99/14226 | 3/1999 |
| WO | WO 99/49081 A2 | 9/1999 |
| WO | WO 00/44934 | 8/2000 |
| WO | WO 00/50869 A2 | 8/2000 |
| WO | WO 01/09374 A2 | 2/2001 |
| WO | WO 01/38565 A2 | 5/2001 |
| WO | WO 01/42493 A2 | 6/2001 |
| WO | WO 01/76451 A2 | 10/2001 |
| WO | WO 02/36821 A2 | 5/2002 |
| WO | WO 02/38801 | 5/2002 |
| WO | WO 02/46452 | 6/2002 |
| WO | WO 02/072880 | 9/2002 |
| WO | WO 02/097065 | 12/2002 |
| WO | WO 03/008623 A2 | 1/2003 |
| WO | WO 03/048732 | 6/2003 |
| WO | WO 03/051901 A2 | 6/2003 |
| WO | WO 03/052132 A2 | 6/2003 |
| WO | WO 03/052133 A2 | 6/2003 |
| WO | WO 03/052134 A2 | 6/2003 |
| WO | WO 2004/015139 | 2/2004 |
| WO | WO 2004/065625 | 8/2004 |
| WO | WO 2006/113770 A1 | 8/2004 |
| WO | WO 2004/090166 | 10/2004 |
| WO | WO 2004/096825 | 11/2004 |
| WO | WO 2004/111266 A | 12/2004 |
| WO | WO 2005/021778 | 3/2005 |
| WO | WO 2005/056790 A1 | 6/2005 |
| WO | WO 2005/113760 A2 | 12/2005 |
| WO | WO 2006/058393 | 6/2006 |
| WO | WO 2006/066353 | 6/2006 |
| WO | WO 2006/113770 A1 | 10/2006 |
| WO | WO 2006/125267 | 11/2006 |
| WO | WO 2007/106802 A2 | 9/2007 |
| WO | WO 2008/109945 A1 | 9/2008 |
| WO | WO 2008/135512 A2 | 11/2008 |
| WO | WO 2008/150998 | 12/2008 |
| WO | WO 2009/070843 | 6/2009 |
| WO | WO 2009/079703 | 7/2009 |

OTHER PUBLICATIONS

Cohen, Y. et al, "Hypermethylation of CpG Island Loci of Multiple Tumor Suppressor Genes in Retinoblastoma", Experimental Eye Research, 2008, vol. 86, No. 2, pp. 201-206.

Shibutani, S. et al. "Translesional Synthesis on DNA Templates Containing a Single Abasic Site", The Jourrial of Biological Chemistry, 1997; vol. 272, No. 21, pp. 13916-13922.

Triplett, J. W. et al., Carbon-13 NMR Investigation of the bisulphite induced changes in yeast RNA; Biochemical and Biophysical Research Communications (1977), vol. 77, No. 4, pp. 1170-1175.

Shiraishi, M. et al. High Speed Conversion of Cytosine to Uracil in Bisulphite Genomic Sequencing Analysis of DNA Methylation; DNA Research (2004) vol. II, pp. 409-415.

Grunau, C. et al. Bisulphite genomic sequencing: systematic investigation of critical experimental parameters. Nucleic Acids Research (2001) vol. 29, No. 13, e65.

Munson, K. et al. Recovery of bisulphite-converted genomic sequences in the methylation-sensitive QPCR. Nucleic Acids Research (2007) vol. 35, No. 9, pp. 2893-2903.

Frommer, M. A genomic sequencing protocol that yields a positive display of 5-methylcytosine residues in individual DNA strands. Proc. Nat. Acad. Sci. USA (1992) vol. 89, pp. 1827-1831.

Bakker et al. JBC, vol. 277, No. 25, pp. 22573-22580, Jun. 2002.

Lee et al., Cancer Epidemiology, Biomarkers, Prevention, vol. 6, pp. 443-450, Jun. 1997.

Esteller et al., Cancer Research, vol. 58, pp. 4514-4518, Oct. 1998.

Virmani et al., Clinical Cancer Research, vol. 7, No. 3, pp. 584-489, Mar. 2001.

Melki et al., Cancer Research, vol. 59, pp. 3730-3740, Aug. 1999.

Toyota et al., Cancer Research, vol. 59, pp. 4535-4541, Sep. 1999.

Shao-Qing et al., Chinese Journal of Agricultural Biotechnology, vol. 4, No. 1, pp. 75-79, 2007.

Pao et al., Human Molecular Genetics, vol. 10, No. 9, pp. 903-910, 2001.

Cameron et al., Blood, vol. 94, No. 7, pp. 2445-2451, Oct. 1999.

Tsuda et al., Gynecologic Oncology, vol. 91, pp. 476-485, 2003.

Feng et al.: "Detection of hypermethylated genes in women with and without cervical neoplasia." Journal Of The National Cancer Institute Feb. 16, 2005, vol. 97, No. 4, Feb. 16, 2005, pp. 273-282.

Grigoriev et al., "A Triple Helix-forming Oligonucleotide-Intercalator Conjugate Acts as a Transcriptional Repressor via Inhibition of NFkB Binding to Interleukin-2 Receptor ÿ-Regulatory Sequence. "Journal of Biological Chemistry, 267 (5): 3389-3395 (1992).

Grunau, et al., "Bisulfite genomic sequencing: systematic investigation of critical experimental parameters." Nucleic Acid Research, (2001) vol. 29, No. 13e65, pp. 1-7.

Gu W. et al, Depletion of Saccharomyces cerevisiae tRNAHis Guanylyltransferase Thg1p leads to uncharged tRNAH is with additional m5C, Mol Cell Biol. Sep. 2005; vol. 25, No. 18, pp. 8191-8201.

Hakelien et al., "Reprogramming fibroblasts to express T-cell functions using cell extracts." Nature Briotechnology, 20(5): 460-466 (2002).

Kalantari, Mina et al. "Conserved methylation patterns of human papillomavirus type 16 DNA in asymptomatic infection and cervical neoplasia," *Journal of Virology*, vol. 78, No. 23, Dec. 2004, pp. 12762-12772.

Kim T.Y et al: "DNA hypermethylation in gastric cancer" Alimentary Pharmacology & Therapeutics, vol. 20, No. Suppl. 1, Jul. 2004, pp. 131-142.

Kozak et al.: "Influence of secondary structure on binding and migration of 40S ribosomal subunits," CELL, vol. 19, 1980, pp. 79-90.

Malyukova A.V et al: "Methylation of the Putative Tumor Suppressor Gene RASSF1A in Primary Cervical Tumors" Molecular Biology, Kluwer Academic Publishers-Plenum Publishers, NE, vol. 38, No. 6, Nov. 1, 2004, pp. 857-864.

Narayan, Gopeshwar et al: "Frequent Promoter Methylation of CDH1, DAPK, RARB, and HIC1 Genes in Carcinoma of Cervix Uteri: Its Relationship to Clinical Outcome" Molecular Cancer, Biomed Central, London, GB, vol. 2, No. 1, May 13, 2003, p. 24.

Nousbaum, J. et al., "Prospective Characteristics of Full-Length Hepatitis C Virus NS5A Quasispecies during Induction and Combination Antiviral Therapy," Journal of Virology, 74, No. 19, pp. 9028-9038 (2000).

Asseline et al. Synthesis and binding properties of oligonucleotides covalently linked to an acridine derivative: New study of the influence of the dye attachment site. *Bioconjugate Chem.*, 7:369-379 (1996).

Bleczinski et al. Steroid-DNA interactions increasing stability, sequence-selectivity, DNA/RNA discrimination, and hypochromicity of oligonucleotide duplexes. *J. Am. Chem. Soc.* 121:10889-10894 (1999).

(56) References Cited

OTHER PUBLICATIONS

Burmeister et al. Synthesis of novel phosphoramidite derivatives bearing pyrenyl and dansyl groups. *Tetrahedron Letters.* 36(21):3667-3668 (1995).
De Mesmaeker et al. Amide backbone modifications for antisense oligonucleotides carrying potential intercalating substituents: Influence on the thermodynamic stability of the corresponding duplexes with RNA- and DNA-complements. *Bioorganic & Medicinal Chemistry Letters.* 7(14):1869-1874 (1997).
Francois et al. Recognition of hairpin-containing single-stranded DNA by oligonucleotides containing internal acridine derivatives. *Bioconjugate Chem.*, 1999, 10:439-446.
Herman et al. UNIT 10.6 Methylation-Specific PCR, Current Protocols in Human Genetics, Published Online: May 1, 2001, pp. 10.6.1-10.6.10, DOI: 10.1002/0471142905.hg1006s16, Copyright © 2003 by John Wiley and Sons, Inc: http://onlinelibrary.wiley.com/doi/10.1002/0471142905.hg1006s16/full.
Korshun et al. Reagent for introducing pyrene residues in oligonucleotides. *Bioconjugate Chem.*, 1992, 3:559-562.
Mann et al. Synthesis and properties of an oligodeoxynucleotide modified with a pyrene derivative at the 5'-phosphate. *Bioconjugate Chem.*, 1992, 3:554-558.
Masuko, et al. Fluorescence resonance energy transfer from pyrene to perylene labels for nucleic acid hybridization assays under homogeneous solution conditions. *Nucleic Acids Research*, 28(8):e34, 8 pages (2000).
Paris, et al. Probing DNA sequencs in solution with a monomer-excimer fluorescence color change. *Nucleic Acids Research*, 26(16):3789-3793 (1998).
Timofeev et al. Methidium intercalator inserted into synthetic oligonucleotides. *Tetrahedron Letters.* 37(47):8467-8470 (1996).
Toulmé et al. Specific inhibition of Mrna translation by complementary oligonucleotides covalently linked to intercalating agents. *Proceedings of the National Academy of Sciences of USA.* 83:1227-1231 (1986).
Wang et al. Comparison of bisulfite modification of 5-methyldeoxycytidine and deoxycytidine residues, Nucleic Acids Research, vol. 8 No. 201980, pp. 4777-4790.
Yamana et al. Synthesis and properties of oligonucleotides bearing a pendant pyrene group. *Nucleic Acids Research.* 16:169-172 (1985).
Yamana et al. Oligonucleotides having covalently linked anthracene at specific sugar residue: Differential binding to DNA and RNA and fluorescence properties. *Tetrahedron Letters.* 36(46):8427-8430 (1995).
Yamana et al. Incorporation of two anthraquinonylmethyl groups into the 2'-O-positions of oligonucleotides: Increased affinity and sequence specificity of anthraquinone-modified oligonucleotides in hybrid formation with DNA and RNA. *Bioconjugate Chem.*, 7:715-720 (1996).
Yamana et al. Synthesis of oligonucleotide derivatives containing pyrene labeled glycerol linkers: enhanced excimer fluorescence on binding to a complementary DNA sequence. *Tetrahedron Letters.* 38(34): 6051-6054 (1997).
Yamana et al. 2'-Pyrene modified oligonucleotide provides a highly sensitive fluorescent probe of RNA. *Nucleic Acids Research.* 27(11):2387-2392 (1999).
International Search Report issued in PCT Application No. PCT/AU2004/000083, mailed Feb. 24, 2004.
International Search Report issued in PCT Application No. PCT/AU2004/000549, mailed Jul. 23, 2004.
International Search Report issued in PCT Application No. PCT/AU2004/000722, mailed Jun. 29, 2004.
International Search Report issued in PCT Application No. PCT/AU2004/001196, mailed Sep. 27, 2004.
International Preliminary Report on Patentability in PCT Application No. PCT/AU2006/000698, dated Apr. 20, 2007.
International Search report issued in PCT Application No. PCT/AU2008/001751, mailed Feb. 18, 2009.
International Search Report issued in PCT Application No. PCT/AU2010/000055, mailed Mar. 18, 2010.
International Preliminary Report on Patentability and Written Opinion issued in PCT Application No. PCT/AU2010/000055 mailed Oct. 11, 2010.
Extended European Search Report issued on Mar. 12, 2009 in European Patent Application No. EP 05813335.6.
Office Action in U.S. Appl. No. 10/561,029 dated Dec. 8, 2009.
Office Action in U.S. Appl. No. 10/555,465 dated Oct. 1, 2008.
Notice of Abandonment in U.S. Appl. No. 10/555,465 dated Jun. 2, 2009.
Notice of Allowance in U.S. Appl. No. 10/428,310 dated May 24, 2007.
Notice of Allowance in U.S. Appl. No. 10/428,310 dated Sep. 21, 2007.
Office Action in U.S. Appl. No. 12/413,380 dated Mar. 11, 2011.
Office Action in U.S. Appl. No. 12/413,380 dated Nov. 3, 2011.
Notice of Allowance in U.S. Appl. No. 12/413,380 dated Jan. 9, 2012.
Notice of Abandonment in U.S. Appl. No. 10/416,637 dated Jun. 15, 2007.
Office Action in U.S. Appl. No. 10/499,479 dated Dec. 20, 2006.
Office Action in U.S. Appl. No. 10/499,479 dated Apr. 19, 2007.
Office Action in U.S. Appl. No. 10/499,479 dated Jan. 3, 2008.
Office Action in U.S. Appl. No. 10/499,479 dated May 2, 2008.
Office Action in U.S. Appl. No. 10/499,479 dated May 30, 2008.
Office Action in U.S. Appl. No. 10/499,479 dated Feb. 5, 2009.
Notice of Abandonment in U.S. Appl. No. 10/499,479 dated Nov. 6, 2009.
Office Action in U.S. Appl. No. 12/534,743 dated May 14, 2010.
Notice of Abandonment in U.S. Appl. No. 12/534,743 dated Jan. 5, 2011.
Office Action in U.S. Appl. No. 11/660,586 dated Aug. 6, 2010.
Office Action in U.S. Appl. No. 11/660,586 dated Jul. 20, 2011.
Notice of Abandonment in U.S. Appl. No. 11/660,586 dated Mar. 7, 2012.
Notice of Abandonment in U.S. Appl. No. 10/536,633 dated Jan. 18, 2008.
Office Action in U.S. Appl. No. 11/919,443 dated Feb. 2, 2012.
Office Action in U.S. Appl. No. 11/919,443 dated May 29, 2012.
Office Action in U.S. Appl. No. 10/543,017 dated Aug. 8, 2007.
Notice of Abandonment in U.S. Appl. No. 10/543,017 dated Jun. 26, 2009.
Office Action in U.S. Appl. No. 10/570,715 dated Dec. 14, 2009.
Office Action in U.S. Appl. No. 11/756,534 dated Feb. 22, 2010.
Office Action in U.S. Appl. No. 11/756,534 dated Oct. 20, 2010.
Notice of Abandonment in U.S. Appl. No. 11/756,534 dated May 12, 2011.
Office Action in U.S. Appl. No. 12/531,482 dated Jan. 17, 2012.
Office Action in U.S. Appl. No. 12/066,644 dated Sep. 23, 2010.
Office Action in U.S. Appl. No. 12/066,644 dated Mar. 13, 2012.
Notice of Abandonment in U.S. Appl. No. 12/227,962 dated Sep. 28, 2011.
Office Action in U.S. Appl. No. 12/747,483 dated Feb. 28, 2012.
Office Action in U.S. Appl. No. 12/747,483 dated Jun. 26, 2012.
Badal Sushma et al.: "The human papillomavirus-18 genome is efficiently targeted by cellular DNA methylation" VIROLOGY, vol. 324, No. 2, Jul. 1, 2004, pp. 483-492.
Badal V. et al.: "CpG methylation of human papillomavirus type 16 DNA in cervical cancer cell lines and in clinical specimens: Genomic hypomethylation correlates with carcinogenic progression" Journal Of Virology, The American Society for Microbiology, US, vol. 77, No. 11, Jun. 1, 2003, pp. 6227-6234.
Baleriola C et al.: "Comparison of a novel HPV test with the Hybrid Capture II (hcII) and a reference PCR method shows high specificity and positive predictive value for 13 high-risk human papillomavirus infections" Journal of Clinical Virology, Elsevier, Amsterdam, NL, vol. 42, No. 1, May 1, 2008, pp. 22-26.
Christensen et al., "Intercalating nucleic acids containing insertions of 1-0-(1-pyrenylmethyl) glycerol: stabilisation of dsDNA and discrimination of DNA over RNA." Nucleic Acid Res. vol. 30, No. 22, pp. 4918-4925, (2002).
Clark et al., "High sensitivity mapping of methylated cytosines." Nucleic Acids Research, 22(15): 2990-2997 (1994).

(56) References Cited

OTHER PUBLICATIONS

Clark, et al., "Bisulphite genomic sequencing of methylated cytosines." Laboratory Methods for the Detection of Mutations and Polymorphisms in DNA. Graham R. Taylor, Ed. CRC Press, New York (1997), pp. 151-162.
Cottrell et al., A real-time PCR assay for DNA-methylation-specific blockers. Nucleic Acid Research, 32(1):e10 (8 pages). Jan. 13, 2004.
Dean et al., "Comprehensive human genome amplification using multiple displacement amplification." PNAS, 99(8): 5261-5266 (2002).
Eads et al., "MethylLight: a high-throughput assay to measure DNA methylation." Nucleic Acids Research, 28(8)e32: i-viii (2000).
Extended European Search Report issued in corresponding European Application No. 05779000.8, dated Nov. 24, 2008.
Extended European Search Report issued in corresponding European Application No. 05821631.8, dated Oct. 16, 2008.
Feil et al., "Methylation analysis on individual chromosomes: improved protocol for bisulphite genomic sequencing." (1994) Nucleic Acids Research 22(4): 695-696.
Hakelien et al., "Novel approaches to transdifferentiation", Cloning and Stem Cells, 4: 379-387 (2002).
Herman, et al., "Methylation-specific PCR-: a novel PCR assay for methylation status of CpG islands." (1996) Proc. Natl. Acad. Sci. 93:9821-9826.
Hitchcock, T.M. et al, "Cleavage of deoxyoxanosine-containing oligodeoxyribonucleotides by bacterial endonuclease V", Nucleic Acids Research, 2004, vol. 32, No. 13, pp. 4071-4080.
Hosono et al. "Unbiased Whole-Genome Amplification Directly from Clinical Samples." *Genome Research*; 13:954-964 (2003).
International Human Genome Sequencing Consortium, "Initial sequencing and analysis of the human genome," Nature, 409(6822): 860-921 (2001).
International Preliminary Report on Patentability corresponding to PCT Application No. PCT/AU2008/000367, dated May 6, 2009.
International Search Report corresponding to PCT Application No. PCT/AU2008/000367, dated May 14, 2008.
International Search Report issued in corresponding PCT Application No. PCT/AU2008/001891, mailed Feb. 3, 2009.
International Search report issued in PCT Application No. PCT/AU2008/001796, mailed Feb. 23, 2009.
International Search Report issued on corresponding PCT Application No. PCT/AU2006/000698, dated Aug. 1, 2006.
International Search Report issued on corresponding PCT Application No. PCT/AU2006/000755, dated Aug. 30, 2006.
Kinoshita et al., "Methylation of the androgen receptor minimal promoter silences transcription in human prostate cancer." Cancer Research, 60(13): 3623-3630 (Jul. 1, 2000).
Kono, "Nuclear transfer and reprogramming." Reviews of Reproduction, vol. 2 No. 2, pp. 74-80 (May 1997).
Longo, M.C. et al., "Use of Uracil DNA Glycosylase to Control Carry-Over Contamination in Polymerase Chain Reactions", Gene, vol. 93, No. I, pp. 125-128, Sep. 1990.
Millar et al., "A distinct sequence (ATAAA)n separates methylated and unmethylated domains at the 5'-end of the GSTPI CpG island," J. Biol. Chem., 275(32): 24893-24899 (2000).
Millar et al., "Detailed methylation analysis of the glutathione S-transferase pi (GSTPI) gene in prostate cancer," Oncogene 18(6): 1313-1324, (1999).
Monk, "Epigenetic programming of differential gene expression in development and evolution" Dev. Genetics, vol. 17, pp. 183-197 (1995).
NCBI Database Accession No. M24485, Dec. 5, 1994.
Newton et al., "The production of PCR products with 5' single-stranded tails using primers that incorporate novel phosphoramidite intermediates." Nucleic Acid Res. vol. 21 No. 5, pp. 1155-1162 (1993).
Nilsson et al., Padlock Probes: Circularizing Oligonucleotides for Localized DNA Detection. Science; 265:2085-2088 (1994).
Notice of Allowance issued in U.S. Appl. No. 10/561,029 dated May 28, 2010.
Notice of Allowance issued in U.S. Appl. No. 10/570,715, mailed Jul. 30, 2010.
Notice of Allowance issued in U.S. Appl. No. 11/575,060, mailed Jun. 15, 2010.
Notice of Allowance issued in U.S. Appl. No. 11/573,873, mailed Jul. 1, 2010.
Office Action in U.S. Appl. No. 10/416,637 dated May 4, 2006.
Office Action in U.S. Appl. No. 10/428,310 dated Aug. 31, 2006.
Office Action in U.S. Appl. No. 10/428,310 dated Jan. 4, 2006.
Office Action in U.S. Appl. No. 10/428,310 dated Jul. 5, 2006.
Office Action in U.S. Appl. No. 10/428,310 dated Nov. 3, 2006.
Office Action in U.S. Appl. No. 10/536,633 dated Apr. 4, 2007.
Office Action in U.S. Appl. No. 10/536,633 dated Jan. 25, 2007.
Office Action in U.S. Appl. No. 10/543,017 dated Dec. 8, 2008.
Office Action in U.S. Appl. No. 10/543,017 dated Jun. 20, 2008.
Office Action in U.S. Appl. No. 10/543,017 dated Oct. 19, 2007.
Office Action in U.S. Appl. No. 10/561,029 Dated Apr. 13, 2009.
Office Action in U.S. Appl. No. 10/570,715 dated Apr. 15, 2010.
Office Action in U.S. Appl. No. 11/573,873 dated Mar. 23, 2010.
Office Action in U.S. Appl. No. 11/573,873 dated May 4, 2009.
Office Action in U.S. Appl. No. 11/573,873 dated Sep. 2, 2009.
Office Action in U.S. Appl. No. 11/660,586 dated Apr. 15, 2010.
Office Action in U.S. Appl. No. 11/660,586 dated Sep. 15, 2009.
Office Action in U.S. Appl. No. 11/756,534 dated Aug. 10, 2009.
Office Action in U.S. Appl. No. 11/756,534 dated Jun. 8, 2010.
Office Action in U.S. Appl. No. 12/066,644 dated Apr. 22, 2010.
Okada et al., "Sequence Determination of Rat U5 RNA Using a Chemical Modification Procedure for Counteracting Sequence Compression." (1982) J. Biochem. 91: 1281-1291.
Olek et al. "A modified and improved method for bisulphate based cytosine methylation analysis." (1996) Nucleic Acids Research, 24(24): 2065-5066.
Paulin et al., "Urea improves efficiency of bisulphite-mediated sequencing of 5'-methylcytosine in genomic DNA." Nucleic Acid Research, 26(21): 5009-5010 (Nov. 1, 1998).
Pietrobono et al., "Quantitative analysis of DNA demethylation and transcriptional reactivation of the FMR1 gene in fragile X cells treated with 5-azadeoxycytidine." Nucleic Acids Research, 30(14): 3278-3285 (2002).
Raizis et al.,"A Bisulfite method of 5-methylcytosine mapping that minimizes template degradation", Anal. Biochem., 226: 161-166 (1995).
Ratushna V.G. et al.: "Secondary structure in the target as a confounding factor in synthetic oligomer microarray design," BMC GENOMICS, vol. 6, No. 1, Mar. 2005, p. 31.
Rein et al., "Identifying 5-methylcytosine and related modifications in DNA genomes." Nucleic Acids Research, 26 (10): 2255-2264 (May 15, 1998).
Robertson et al. "DNA methylation: past, present, and future directions." Carcinogenesis. 21(3): 461-467 (2000).
Robertson et al., "Methylation of the Epstein-Barr virus genome in normal lymphocytes", Blood, 90: 4480-4484 (1997).
Sakaguchi et al. "Cautionary Note on the Use of dUMP-Containing PCR Primers with *Pfu* and Vent$_R$ ® DNA Polymerases." *Biotechniques*; 21(3):368 & 370 (1996).
Sakashita et al., "Dynamic DNA methylation change in the CpG island region of p15 during human myeloid development", J. Clin. Invest., 108: 1195-1204 (2001).
Shapiro et al., "Deamination of cytosine derivatives by bisulfite. Mechanism of the reaction," J. Am. Chem. Soc., 96: 906-912 (1974).
Shibutani, S. et al, "Translesional Synthesis on DNA Templates Containing a Single Abasic Site", The Journal of Biological Chemistry, 1997; vol. 272, No. 21, pp. 13916-13922.
Specification and Preliminary Amendment from co-pending U.S. Appl. No. 10/555,465, filed Aug. 28, 2006.
Stratagene, 1988, Catalog, p. 39.
Supplementary European Search Report issued on corresponding European Patent Application No. EP 06 77 4977, dated Jul. 28, 2009.
Tada et al., "Embryonic germ cells induce epigenetic reprogramming of somatic nucleus in hybrid cells." The EMBO Journal, 16(21): 6510-6520 (1997).

(56) References Cited

OTHER PUBLICATIONS

Telenius et al., "Degenerate Oligonucleotide-Primed PCR: General Amplification of Target DNA by a Single Degenerate Primer." *Genomics*; 13(3):718-725 (1992).

Tohgi et al., "Decrease with age in methylcytosines in the promoter region of receptor for advanced glycated end products (RAGE) gene in autopsy human cortex," Molecular Brain Research, 65:124-128 (1999).

Ushijima Toshikazu et al.: "Aberrant Methylations in Cancer Cells: Where Do They Come From?" Cancer Science, vol. 96, No. 4, Apr. 2005, pp. 206-211.

Venter et al., "The Sequence Of the Human Genome," Science, vol. 291 (5523): pp. 1304-1351, (2001).

Verma M: "Viral Genes and Methylation" Annals of the New York Academy of Sciences 200303 US, vol. 983, Mar. 2003, pp. 170-180.

Warnecke et al., "Detection and measurement of PCR bias in quantitative methylation analysis of bisulphite-treated DNA," Nucleic Acids Research, vol. 25 No. 21, pp. 4422-4426, (1997).

Widschwendter et al.: "Analysis of Aberrant DNA Methylation And Human Papillomavirus DNA in Cervicovaginal Specimens To Detect Invasive Cervical Cancer and Its Precursors" Clinical Cancer Research, The American Association for Cancer Research, US, vol. 10, No. 10, May 15, 2004, pp. 3396-3400.

Xiong et al., "COBRA: a sensitive and quantitative DNA methylation assay." (1997) Nucleic Acids Research, 25 (12): 2532-2534.

Yanagi et al., "Hepatitis C Virus: An Infectious Molecular Clone of a Second Major Genotype (2A) and Lack of Viability of Intertypic 1A and 2A Chimeras," Virology 262, pp. 250-263 (1999).

Yao, M. et al, "Further Characterization of *Escherichia coli* Endonuclease V", Journal of Biological Chemistry, 1997, vol. 272, No. 49, pp. 30774-30779.

Zeschnigk et al., "A novel real-time PCR assay for quantitative analysis of methylated alleles (QAMA): analysis of the retinoblastoma locus," Nucleic Acid Research 2004, vol. 32, No. 16, pp. 1-5.

D'Abbadie, et al., "Molecular Breeding of Polymerases for Amplification of Ancient DNA," *Nature Biotechnology*, (Aug. 2007) 25:939-943.

Supplemental European Search Report issued on Dec. 21, 2010 in corresponding European Patent Application No. EP 08853330.2.

Edamoto et al., Alterations of RB1, p53 and Wnt Pathways in Hepatocellular Carcinomas Associated with Hepatitis C, Hepatitis B and Alcoholic Liver Cirrhosis, Int J Cancer (2003) 106: 334-341.

Shapiro et al., Specific Deamination of RNA by Sodium Bisulphite, Nature (1970) 227: 1047-1048.

Office Action in U.S. Appl. No. 12/744,310 dated Aug. 20, 2012.

\* cited by examiner

2A

2B

2C

2D

ENZYMES FOR AMPLIFICATION AND COPYING BISULPHITE MODIFIED NUCLEIC ACIDS

RELATED APPLICATIONS

This application is the U.S. National Phase filing under 35 U.S.C. §371 of PCT/AU2008/001751, filed Nov. 27, 2008, entitled "Enzymes for Amplification and Copying Bisulphite Modified Nucleic Acids", which designated the United States and was published in English on Jun. 4, 2009 as WO 2009/067743, which claims priority under 35 U.S.C. §119(a)-(d) to Australian Patent Application No. 2007906490, filed Nov. 27, 2007.

TECHNICAL FIELD

The present invention relates to use of enzymes for copying or amplifying nucleic acids, particularly nucleic acids treated with bisulphite.

BACKGROUND ART

As a result of advances in automated sequencing technology, much work has been carried out on determining coding regions of DNA resulting in the full sequencing of many animal genomes including the human genome. It has been realised for many years that the majority of genomic DNA, however, is non-coding and this materiel was once considered as "junk" DNA. Analysis of the non-coding regions of DNA is now being considered as important in the study of gene expression and function. Methylation states or patterns in nucleic acid, particularly genomic DNA, is thought to have a functional or regulatory role in gene expression and control in animals.

It has been demonstrated that, in single stranded DNA, sodium bisulphite preferentially deaminates cytosine to uracil, compared to a very slow rate of deamination of 5-methylcytosine to thymine (Shapiro, R., DiFate, V., and Welcher, M, (1974) J. Am. Chem. Soc. 96: 906-912). This observation served as the basis for the development of the bisulphite genomic sequencing protocol of Frommer et al 1992 (Frommer M, McDonald L E, Millar D S, Collis C M, Watt F, Grigg G W, Molloy P L and Paul C L. PNAS 89: 1827-1831 (1992)). In summary, this method as presently practiced involves the following general steps: alkaline denaturation of DNA; deamination using sodium bisulphite; desulphonation by desalting followed by sodium hydroxide treatment; neutralization and desalting.

One of the major disadvantages of the bisulphite modification procedure and the established variation thereof is that it has been shown that the procedure results in the degradation of between 84-96% of the original input DNA (Grunau et al. Nucleic Acids Research 29 (13) e65, (2001)). The high loss associated with the procedure means that practically it is very difficult to successfully analyse small numbers of cells for their genomic methylation status, or successfully analyse ancient archival specimens in which the DNA is already in a partially degraded state. In addition, due to inherent nucleic acid degradation of the current methods, it is not possible to sequence and assemble the complete genome of an organism to determine its genome-wide methylation profile in the same manner as has been successfully applied by the public Human Genome Project (International Human Genome Sequencing Consortium, 2001, Nature, 409, 860-921) or the private CEL-ERA sequencing project (J Craig Venter et al., 2001, Science, 291, 1304-1351) owing to the huge number of "gaps" in the sequence.

A further disadvantage with the bisulphite method as presently practiced is that, in general, only small fragments of DNA can be amplified. Experience shows that generally less than about 500 base pairs (bp) can be successfully treated and amplified. The present technique is not applicable to new molecular biological methods such as Long Distance polymerase chain reaction (PCR) which has made it possible to amplify large regions of untreated genomic DNA, generally up to about 50 kb. At present, it is not even possible to analyse the methylation status of intact genes, as a large number of genes in mammalian genomes exceed 50 kb in length.

Thermostable polymerases in widespread use are unable to bypass the abasic sites generated during the bisulphite conversion and generally this causes stalling of the amplification reaction (Sikorsky, J. A., Primerano, D. A., Fenger, T. W. and Denvir, J. (2004) Biochem. Biophys. Res. Commun. 323, 823-230). In addition, these polymerases are also unable to successfully and efficiently amplify DNA which contains bulky adducts such as sulphonate groups. This necessitates desulphonation of the bisulphite converted nucleic acid at high temperatures in an alkaline medium prior to PCR amplification and results in the majority of the nucleic acid damage and lass seen during this procedure (Munson, K., Clark, J., Lamparska-Kupsik, K. and Smith, S. S. (2007) Nucl. Acids. Res. 35(9), 2893-2903). Furthermore, the generation of effectively a T-rich 3 base genome (as non-methylated C's are converted to U's and then into Ts during PCR amplification, giving rise to a genome comprised predominantly of bases A, T, G) results in significant difficulties for currently available polymerases and causes frequent slippage during extension. An additional problem encountered during PCR amplification of bisulphite converted DNA is that the single stranded template contains uracil which some polymerases, such as the archaebacterial DNA polymerases like Pfu Pwo and Vent, are unable to process (Lasken, R. S., Schuster, D. M. and Rashtchian, A. (1996) J. Biol. Chem. 271 (30), 17692-17696). Currently, therefore, in order to investigate the methylation status of even relatively small genes (<4 kb), PCR reactions have had to be staggered across the gene region of interest (D. S Millar, K. K Ow, C. L. Paul, P. J. Russell, P. L. Molloy, S. J. Clarke, 1999, Oncogene, 18(6):1313-24; Millar D S, Paul C L, Molloy P L, Clarke S J. (2000). J Biol Chem; 275(32): 24893-9).

In some instances it is desirable to bisulphite modify RNA prior to reverse transcription into cDNA and subsequent PCR. However, RNA is even more sensitive to degradation at the high temperatures and pH required for desulphonation and this results in a further reduction in sensitivity. There is a need for enzymes that are capable of efficiently processing bisulphite modified, treated or converted nucleic acids.

DISCLOSURE OF INVENTION

The present inventor has surprisingly found that it is possible to identify or modify enzymes which are more effective in their ability to efficiently process bisulphite modified or treated nucleic acid.

The present invention generally relates to use of new or modified enzymes which are more effective in their ability to copy or amplify bisulphite modified or treated nucleic acid than currently available enzymes such as the eubacterial enzyme Taq polymerase, Superscript III reverse transcriptase, Klenow exo-polymerase, Bst polymerase or Bca polymerase under substantially the same reaction conditions.

In a first aspect, the invention provides use of an enzyme for copying or amplifying bisulphite modified or treated nucleic acids, wherein the enzyme is more effective in copying or amplifying the nucleic acid compared with native Taq polymerase under substantially the same conditions.

Preferably, the enzyme is capable of copying or amplifying nucleic add having abasic sites, bulky adducts such as sulphonate groups, substantially only having A, T, G and U bases, or substantially only having A, T and G bases.

The enzymes can be a thermophilic or mesophilic polymerase, a reverse transcriptase, an endonuclease or modified or chimeric forms thereof.

Preferably, the enzyme is selected from enzymes described in EP 18012113, 5D4 as herein defined, HIV-RT, and modified forms thereof.

Enzymes suitable for use in the present invention maybe obtained using the modification methods disclosed in WO 99/02671, WO 00140712, WO 02/22869, WO 03/044187, WO 05/045 and EP 18012113 (Medical Research Council) incorporated herein by reference.

In a second aspect, the present invention provides a method for copying or amplifying bisulphite treated nucleic acid comprising:

bisulphite treating a nucleic acid; and copying or amplifying the bisulphite treated nucleic acid using an enzyme which is more effective in copying or amplifying bisulphite treated nucleic acid compared with native Taq polymerase under substantially the same conditions.

Preferably the bisulphite treatment uses sodium bisulphite or sodium metabisulphite.

Preferably the bisulphite treatment is substantially without a desulphonation step.

Preferably the method further comprising denaturing the nucleic acid prior to bisulphite treatment.

Preferably the denaturing step is carried out by providing an alkali environment or heating the nucleic acid.

Preferably any methylated nucleotides in the sample remain unchanged while unmethylated nucleotides are converted to uracil by the bisulphite treatment.

Preferably the method further comprises desalting or isolating the treated nucleic acid sample.

Preferably the enzyme is capable of copying or amplifying nucleic acid having abasic sites, bulky adducts including sulphonate groups, having substantially only A, T, G and U bases, or substantially only having A, T and G bases.

Preferably the enzyme is selected from the group consisting of thermophilic polymerase, mesophilic polymerase, reverse transcriptase, endonuclease, and modified and chimeric forms thereof.

In a preferred form, the enzyme is selected from chimeric enzymes, 5D4 as herein defined, HIV-RT, and modified forms thereof.

In a preferred form, the enzyme is 5D4 or modified forms thereof.

In a preferred form, the enzyme is HIV-RT or modified forms thereof.

Preferably the method further comprises processing or analysing the treated nucleic acid to determine nucleotide sequence, methylation status, identify of source of nucleic acid, or detect a microorganism.

Preferably the amplification of the bisulphite treated nucleic acid is carried out by polymerase chain reaction (PCR), Reverse-Transcriptase PCR, qPCR, isothermal amplification, or signal amplification.

Preferably the treated nucleic acid comprises bisulphite modified DNA, bisulphite modified RNA, or a combination of bisulphite modified DNA and bisulphite modified RNA.

In a third aspect, the present invention provides a method for copying or amplifying bisulphite treated nucleic acid comprising:

denaturing a nucleic acid sample;

treating the nucleic acid sample with a bisulphite reagent and incubating the sample to form a treated nucleic acid sample where any methylated nucleotides in the sample remain unchanged while unmethylated nucleotides are converted to another form;

desalting or isolating the treated nucleic acid sample; and using an enzyme which are more effective in their ability to efficiently process bisulphite modified or treated nucleic acid to amplify, reverse transcribe, digest, or otherwise enzymatically process the bisulphite modified nucleic acid.

The method may further comprise:

processing or analysing the treated nucleic acid to determine nucleotide sequence or methylation status.

Amplification of bisulphite treated nucleic acid can be carried out by any suitable means such as polymerase chain reaction (PCR), Reverse-Transcriptase PCR, qPCR, isothermal amplification, or signal amplification.

Preferably, the denaturing step is carried out by providing an alkali environment or heating the nucleic acid sample.

Preferably, the treated nucleic acid comprises bisulphite modified DNA, bisulphite modified RNA, or a combination of bisulphite modified DNA and bisulphite modified RNA.

The sample can be obtained from tissue, organ, cell, microorganism, biological sample, or environmental sample. Preferably, the tissue or organ is selected from brain, colon, urogenital, lung, renal, hematopoietic, breast, thymus, testis, ovary, uterus, or mixtures thereof. Preferably, the microorganism is selected from bacteria, virus, fungi, protozoan, viroid, or mixtures thereof. Preferably, the biological sample is selected from the group consisting of blood, urine, faeces, semen, cerebrospinal fluid, lavage or mixtures thereof.

Unlike prior art methods, the method uses enzymes, including, but not limited to, thermophilic and mesophilic polymerases, reverse transcriptases and endonucleases that will specifically have an enhanced ability to process bisulphite modified nucleic acids compared to currently available enzymes. Primarily, the enzymes will have enhanced function in their ability to bypass abasic sites, bulky adducts on the DNA such as sulphonate groups and to work more effectively on a 3-base genome compared to standard enzymes such as Taq polymerase, Superscript III reverse transcriptase, Klenow exo-polymerase, Bst polymerase or Bca polymerase, but other modifications may also be generated. The generation of new enzymes which are able to process nucleic acids with sulphonate groups attached will abrogate the need to desulphonate the nucleic acid following bisulphite modification and will hence eliminate the damage and loss of nucleic acid seen in current methods, as well as saving time. Furthermore, the use of polymerases that are more capable of bypassing abasic sites will enable more efficient PCR reactions and the generation of longer PCR products than is currently possible using the standard enzymes that are currently available.

Preferably, the bisulphite is sodium bisulphite, a reagent which, in the presence of water, modifies cytosine into uracil.

Sodium bisulphite ($NaHSO_3$) reacts readily with the 5,6-double bond of cytosine to form a sulfonated cytosine reaction intermediate which is susceptible to deamination, and in the presence of water gives rise to uracil sulphonate. If necessary, the sulphonate group can be removed under mild alkaline conditions, resulting in the formation of uracil. Thus, potentially all unprotected cytosines will be converted to uracils. Any methylated cytosines, however, cannot be converted by bisulphite due to protection by methylation.

Bisulphite treatment of DNA results in modified nucleic acid having a reduced total number of cytosines compared with the corresponding untreated nucleic acid where any unmethylated cytosines (C) will be converted to uracil (U). Thus, a bisulphite treated nucleic acid having no methylation wilt substantially contains bases adenine (A), guanine (G), thymine (T) and uracil (U) but still have substantially the same total number of bases as the corresponding untreated nucleic acid. If this treated nucleic acid undergoes amplification, for example by PCR, a simplified form of the nucleic acid is formed with substantially only the bases adenine (A), guanine (G) and thymine (T).

For double stranded DNA which contains cytosines; the bisulphite treatment results in two nucleic acids (one for each complementary strand), each containing the bases adenine, guanine, thymine and uracil. The two nucleic acids are produced from the two single strands of the double stranded DNA. The two nucleic acids can have no cytosines but still have the same total number of bases and sequence length as the original untreated DNA molecule. Importantly, the two treated nucleic acids are not complimentary to each other and form a top and a bottom strand template for amplification. One or more of the strands can be used as the target for amplification or further processing. During amplification of the treated nucleic acids, uracils in the top (or bottom strand) are replaced by thymines in the corresponding amplified product of the nucleic acid. As amplification continues, the top (and/or bottom strand if amplified) will be diluted out as each new complimentary strand will have only bases adenine, guanine, thymine.

In a fourth aspect, the present invention provides use of an enzyme selected from the group consisting of 5D4 or modified forms thereof, or HIV-RT reverse transcriptase or modified forms thereof in a copying or amplifying bisulphite treated nucleic acid.

Preferably, the bisulphite treatment is substantially without a desulphonation step.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia prior to development of the present invention.

In order that the present invention may be more clearly understood, preferred embodiments will be described with reference to the following drawings and examples.

MODE(S) FOR CARRYING OUT THE INVENTION

Enzymes

Figure 1:
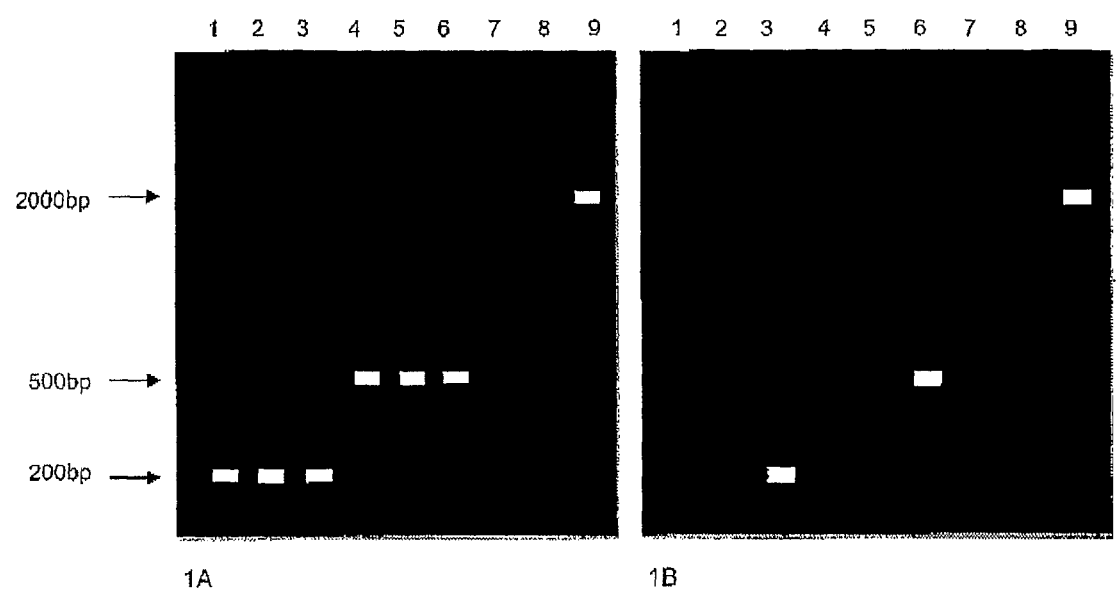
FIG. 1 is a diagram showing expected results of PCR amplification of (Fig A) desulphonated and (Fig B) non-desulphonated bisulphite treated DNA with Taq polymerase (lanes 1, 4 and 7), Dpo4 polymerase (lanes 2, 5 and 8) and a hybrid polymerase (lanes 3, 6 and 9), 10 pg of bisulphite treated DNA was amplified using primers that yield an amplicon of 200 bp (lanes 1-3), 500 bp (lanes 4-6) or 2000 bp (lanes 7-9).

The recently developed technique of compartmentalised self-replication (CSR) or in vitro compartmentalisation (IVC) is one technique which can be manipulated to generate new enzymes with specific characteristics (Tawfik, D. S and Griffiths, A. D. (1998) Nature Biotech. 16, 652-656: Ghadessy, F. J., Ong, J. L. and Holliger, P. (2001) PNAS. 98(8), 4552-4557; d'Abbadie; M., Hofreiter, M., Vaisman, A., Loakes, D., Gasparutto, D., Cadet, J., Woodgate, R., Paabo, S, and Holliger, P. (2007) Nature Biotech. 25(8), 939-943). In addition, new enzymes such as the DinB family of polymerases (Boudsocq, F., Iwai, S., Hanaoke, F. and Woodgate, R. (2001) Nucl. Acids. Res. 29, (22), 4607-4616) which are found in all three kingdoms of life, have been reported that have new properties, which to date have only been exploited for the amplification of ancient DNA, and may be useful for copying or amplifying bisulphite treated nucleic acids.

Examples of enzymes suitable for use in the present invention maybe obtained using the modification methods disclosed in WO 99/42671, WO 00/40712, WO 02/22869, WO 03/044187, WO 05/045 and EP 18012113 (Medical Research Council) incorporated herein by reference.

A number of modified enzymes are disclosed in EP 18012113 which are potential candidates for use in the present invention or be further modified to develop or enhance activity on bisulphate treated nucleic acid. Examples include enzymes designated 2F3, 1A10, 1A9, 2F12, 1C2, 2G6, 1A8, 2F11, 2H4, 2H9, 1B12, 2H2, 1C8, 2H10X, 3A10, 3B5, 3B6, 3B8, 3B10, 3C12. 3D1, 4D1 and 5D4. The enzyme 5D4 has been found by the present inventor to be particularly suitable for the present invention.

Various mutagenesis and/or recombination techniques can be used to generate mutant/hybrid enzymes. Error-prone PCR mutagenesis (Zaccolo, M. and Gherardi, E. (1999) J. Mol. Biol. 285, 775-783), staggered extension process (StEP; Zhao, H., Giver, L., Shao, Z. Afftholter, J. A. and Arnold, F. H. (1998) Nature biotech. 16, 258-261) and molecular breeding (d'Abbadie, M., Hofreiter, M., Vaisman, A., Loakes, D., Gasparutto, D., Cadet, J., Woodgate, R., Paabo, S. and Holliger, P. (2007) Nature Biotech. 25(8), 939-943) are examples of suitable techniques, but other techniques may also be used.

Error-prone PCR mutagenesis is a random process of mutating sequences during a PCR reaction in which the triphosphate derivatives of a pyrimidine (6-(2-deoxy-β-D-ribofuranosyl)-3,4-dihydro-8H-pyrimido-[4,5-c][1,2]oxazin-7-one; dP) and a purine (8-oxo-2'-deoxyguanosine; 8-oxodG) nucleoside analogue are employed in DNA synthesis reactions in vitro and act as mutagenic agents. The primers used are typically biotinylated (or carry a different label) to enable the mutant PCR products to be purified from the wild type DNA, so that the mutated sequences can be cloned and screened for desirable characteristics and then subjected to further rounds of mutagenesis and screening. The procedure yields higher frequencies of amino acid residue substitutions, at least one order of magnitude greater, than those previously achieved.

The staggered extension process (StEP) combines in vitro mutagenesis and recombination of template sequences in a PCR format. The template sequence(s) are primed with common flanking primers and undergo PCR cycling with extremely short annealing and extension steps. The short extension times result in incomplete primer extension during each round. In subsequent cycles, the growing fragments anneal to different templates based on sequence complementarity and extend further, effectively leading to recombination between different genes. The process is continued until full-length sequences are made and fine tuning the extension times gives some control over the length of the gene segments that are swapped.

Molecular breeding has been demonstrated to be superior for the selection of damage-tolerant polymerases than random mutagenesis procedures alone. This procedure utilizes StEP to recombine segments of various polymerases from different organisms. This yields a variety of chimeric polymerases which can then be tested for the desired attributes. This protocol would also be suitable for the generation of other chimeric enzymes such as reverse transcriptases, endonucleases etc.

The enzymes of interest for use with bisulphite modified nucleic acids include, but are not limited to, thermophilic and mesophilic DNA polymerases (for example, Taq, Pfu, Tth, Tfl, Pfx, Pfx50™, Tko, Bst, Bca, Vent$_R$®, Deep Vent™, Phusion™, ABV, UlTima, DyNAzyme EXT™, Therminator, polκ, pol IV, Dbh, Dpo4 and Dpo4-like enzymes, DNA I, Klenow fragment of DNA I polymerase, Klenow exo-, Phi 29, T4 and T7 DNA polymerases), reverse transcriptases (for example, AMV RT, M-MuLV RT, ThermoX RT™, Thermoscript RT™, Superscript III), and endonucleases (for example, Endonuclease III, IV, V, VIII, T7 Endonuclease I, hOGG1, UDG, Fpg, USER) and mutants or chimeras thereof.

New enzymes suitable for the present invention that are superior in their ability to process bisulphite modified DNA or RNA can be made using one or more of the techniques set out above, or a combination of these techniques or other suitable techniques of mutagenesis and/or recombination or by the isolation of new types of polymerases from diverse bacterial species such as the DinB family of polymerases (Boudsocq, F., Iwai, S., Hanaoka, F. and Woodgate, R. (2001) Nucl. Acids. Res. 29, (22), 4607-4616) that have been shown to have unique properties that may be useful when using bisulphite treated nucleic acid samples. In particular, but not exclusively, thermophilic and mesophilic polymerases, reverse transcriptases and endonucleases are targeted. Two or more enzymes from the same class or different classes of enzymes will undergo recombination to yield large numbers of mutant/hybrid enzymes. Hybrid enzymes will be screened and those exhibiting high processivity and high tolerance to DNA damage will be selected and examined further. The assay of choice will depend on the enzyme type being examined. For example, polymerase activity can be assayed for by PCR and comparing the ability of the "new" enzyme to amplify wild-type and a bisulphite modified template with that of the parent polymerases. In this case, clones that exhibit a superior ability to amplify bisulphite modified DNA will be selected for further rounds of recombination and reselection until a polymerase or polymerases exhibiting the ability to efficiently amplify bisulphite converted DNA to a level that is better than the parental polymerases whilst displaying satisfactory levels of processivity and thermostability is generated. The bisulphite modified nucleic acid may or may not be desulphonated.

An example where chimeras of two different enzymes may be beneficial for the amplification of bisulphite modified DNA is the recombination of the thermostable polymerase Taq, which has high processivity but low tolerance to DNA damage, and Dpo4-like enzymes which have low processivity but are capable of replicating past several types of DNA lesions, including abasic sites and bulky adducts (McDonald, J. P., Hall, A., Gasparutto, D., Cadet, J., Ballantyne, J. and Woodgate, R. (2006) 34(4), 1102-1111). Any combination of polymerases, reverse transcriptases, endonucleases, DNA modifying enzymes, and other enzymes, may be recombined together using these techniques and their use in processing bisulphite converted nucleic acids is covered herein by this invention.

Applications

The present invention provides methods for the utilisation of enzymes that have enhanced abilities to process bisulphite modified nucleic acids. The methods are advantageous in that they can identify a new array of enzymes that will be capable, for example, but not limited to, of improved PCR amplification efficiency and increased amplicon length of bisulphite modified DNA, and of efficient reverse transcription and/or one-step reverse-transcription PCR of bisulphite modified RNA. The methods of the present invention provide a simplified procedure by which bisulphite modified nucleic acids can be manipulated using common molecular biological techniques, without the need to de-sulphonate the samples, which will greatly improve yield and maintain higher molecular weight DNA relative to previously known methods. These enzymes, coupled with bisulphite modification techniques, will enable the successful analysis of the methylation state of the genomes in small numbers of cells, of archival nucleic acids and of large stretches of nucleic acids or whole genes, all of which have been hitherto impossible.

The terms "more efficient activity" or "Improved activity" as used herein mean that the isolated enzyme according to the present invention can process bisulphite modified nucleic acid more effectively with less or no substantial errors as compared with standard enzymes presently in use, such as Taq polymerase, Superscript III reverse transcriptase Klenow exo-polymerase, Bst polymerase or Bca polymerase, under substantially the same reaction conditions.

The bisulphite modified sample may include DNA or RNA or a combination of both DNA and RNA.

The sample can be prepared from tissue, cells or can be any biological sample such as blood, urine, faeces, semen, cerebrospinal fluid, lavage, cells or tissue from sources such as brain, colon, urogenital, lung, renal, hematopoietic, breast, thymus, testis, ovary, uterus, tissues from embryonic or extra-embryonic lineages, environmental samples, plants, microorganisms including bacteria, intracellular parasites, virus, fungi, protozoan, viroid and the like. The best described mammalian cell types suitable for treatment by the present invention are summarized in B. Alberts et al., 1989, The Molecular Biology of the Cell, 2nd Edition, Garland Publishing Inc New York and London, pp 995-997.

The analysis of 5-methyl cytosine residues in DNA from samples of human, animal, plant, bacterial, fungal and viral origin is meant to cover all life cycle stages, in all cells, tissues and organs from fertilization until 48 hours post mortem, as well as samples that may be derived from histological sources, such as microscope slides, samples embedded in blocks, or samples extracted from synthetic or natural surfaces or from liquids.

The analyses include the naturally occurring variation between cells, tissues and organs of healthy individuals, (health as defined by the WHO), as well as cells, tissues and organs from diseased individuals. Diseased in this sense includes all human diseases, afflictions, ailments and deviant conditions described or referred to in Harrison's Principles of Internal Medicine, 12th Edition, edited by Jean D Wilson et al., McGraw Hill Inc, and subsequent later editions; as well as all diseases, afflictions ailments and deviant conditions described in OMIM (Online Mendelian Inheritance in Man, www.ncbi.gov), but with emphases on the leading causes of death, namely, malignant neoplasms, (cancer), ischaemic heart disease, cerebrovascular disease, chronic obstructive pulmonary disease, pneumonia and influenza, diseases of arteries, (including atherosclerosis and aortic aneurysm), diabetes mellitus, and central nervous system diseases, together with socially debilitating conditions such as anxiety, stress related neuropsychiatric conditions and obesity, and all conditions arising from abnormal chromosome number or chromosome rearrangements, (aneuploidy involving autosomes as well as sex chromosomes, duplications, deficiencies, translocations and insertions), as well as similar abnormalities of the mitochondrial genomes.

The normal or diseased individuals may be from (i) populations of diverse ethnicity and evolutionary lineages; (ii) strains and geographical isolates; (iii) sub species; (iv) twins or higher order multiplets of the same or different sex; (v) individuals arising from normal methods of conjugation, artificial insemination, cloning by embryonic stem cell methods, or by nuclear transfer, (from somatic or germ line nuclei), or from the input or modification of mitochondrial or other cellular organelles; (vi) individuals deriving from transgenic knock-out, knock-in or knock-down methods, (either in vivo, ex vivo, or by any method in which gene activity is transiently or permanently altered, e.g., by RNAi, ribozyme, transposon activation, drug or small molecule methodologies, Peptide Nucleic Acid (PNA), Intercalating Nucleic Acid (INA), Altritol Nucleic Acid (ANA), Hexitol Nucleic Acid (HNA), Locked Nucleic Acid (LNA), Cyclohexanyl Nucleic Acid (CNA), and the like, or nucleic acid based conjugates, including but not restricted to Trojan peptides, or individuals at any stages of pregnancy, normal or ectopic.

The analyses also include 5-methyl cytosine and cytosine residues in DNA or RNA from prokaryotic or eukaryotic organisms and viruses (or combinations thereof), that are associated with human diseases in extracellular or intracellular modes, for the purposes of diagnostics and disease state monitoring or determining, and therapeutically altering, in both normally varying and diseased systems, the changed parameters and underlying mechanisms of:

(i) genetic diseases;
(ii) non-genetic or epigenetic diseases caused by environmentally induced factors, be they of biological or non-biological origin, (environmental in this sense being taken to also include the environment within the organism itself, during all stages of pregnancy, or under conditions of fertility and infertility treatments);
(iii) predisposition to genetic or non genetic diseases, including effects brought about by the "priori" class of factors, by exposure to pressure changes and weightlessness, or by radiation effects;
(iv) 5-methyl cytosine changes in the processes of aging in all cell types, tissues, organ systems and biological networks, including age related depression, pain, neuropsychiatric and neurodegenerative conditions and pre- and post-menopausal conditions, (including reduced fertility; in both sexes);
(v) 5-methyl cytosine changes in cancer, (including changes in cells with abnormal karyotypes arising from DNA amplification, deletion, rearrangement, translocation and insertion events), and their variations or alterations in different cell cycle phenomena (including cell cycle effects on diurnal rhythms, photoperiod, sleep, memory, and "jet lag";
(vi) 5-methyl cytosine changes in metabolic networks defined in the broadest sense, from the zygote through embryogenesis, foetal development, birth, adolescence, adulthood and old age (including metabolic effects brought about by hypoxia, anoxia, radiation of any type, (be it ionizing or non ionizing, or arising from chemotherapeutic treatments, high altitude exposure radiation from nearby natural sources, such as rocks or from "fallout" from military or government sponsored activities), stress, or by imbalances between the mitochondrial, nuclear or organellar genomes;
(vii) 5-methyl cytosine alterations due to responses at the molecular, cellular, tissue, organ and whole organism levels to proteins, polypeptides, peptide's, and DNA, RNA, PNA, INA, ANA, HNA, LNA, CNA, and the like, or peptide aptamers (including any with post translational additions, post translational cleavage products, post translational modifications (such as inteins and exeins, ubiquination and degradation products); proteins, polypeptides and peptides containing rare natural amino acids, as well as single rare amino acids such as D-serine involved in learning, brain growth and cell death; drugs, biopharmaceuticals, chemical entities (where the definitions of Chemical Entities and Biopharmaceuticals is that of G. Ashton, 2001, Nature Biotechnology 19, 307-3111)), metabolites, new salts, prodrugs, esters of existing compounds, vaccines, antigens, polyketides, non-ribosomal peptides, vitamins, and molecules from any natural source (such as the plant derived cyclopamine);
(viii) 5-methyl cytosine or cytosine alterations due to responses at the molecular, cellular, tissue, organ and whole organism levels to RNA and DNA viruses be they single or double stranded, from external sources, or internally activated such as in endogenous transposons or retrotransposons, (SINES and LINES);
(ix) 5-methyl cytosine alterations due to responses at the molecular, cellular, tissue, organ and whole organism levels to reverse transcribed copies of RNA transcripts be they of genic or non genic origins, (or intron containing or not);
(x) 5-methyl cytosine alterations due to responses at the molecular, cellular, tissue, organ and whole organism levels to: (a) DNA, RNA, PNA, INA, ANA, HNA, LNA, CNA, and the like (or DNA, RNA, PNA, INA, ANA, HNA, LNA, CNA, aptamers of any in all combinations); including DNA, RNA, PNA, INA, ANA, HNA, LNA, CNA, and the like molecules circulating in all fluids including blood and cerebrospinal fluid as well as maternal fluids before, during and after pregnancy (b) combinations of conjugated biomolecules that are chimeras of peptides and nucleic acids; or chimeras of natural molecules such as cholesterol moieties, hormones and nucleic acids; and
(xi) 5-methyl cytosine alterations due to responses of stem cells, (either in vivo, ex vivo or in association with novel environments or natural and synthetic substrates (or combinations thereof), from human and animal origin to any of the perturbations described in (i) to (x) above.

Modified Nucleic Acid

Any suitable method for obtaining nucleic acid material can be used. Examples include, but are not limited to, commercially available DNA, RNA kits or reagents, workstation, standard cell lysis buffers containing protease reagents and organic extraction procedures, which are well known to those of skill in the art.

The method can be carried out in a reaction vessel. The reaction vessel can be any suitable vessel such as tube, plate, capillary tube, well, centrifuge tube, microfuge tube, slide, coverslip, bead, membrane or any suitable surface. The method is generally carried out in one reaction vessel in order to reduce the likelihood of degradation or loss of the nucleic acid sample.

Generally, the alkali environment is provided to the sample by adding an alkali such as NaOH. If the nucleic acid material is RNA then heat is used instead of alkali to produce single stranded material without secondary structure. The alkali environment is provided to denature double stranded nucleic acid molecules into a state where the molecules are readily reactive with the bisulphite reagent. It will be appreciated, however, that any other denaturation method such as heat treatment or other suitable alkali or denaturing agent could be added or used such as KOH and any other alkali.

Bisulphite Treatment

Generally, the bisulphite reagent is sodium metabisulphite. The bisulphite reagent is used to cause sulphonation of cytosine bases to cytosine sulphonate followed by hydrolytic deamination of the cytosine sulphonate to uracil sulphonate. It will be appreciated, however, that any other suitable bisulphite reagent could be used such as sulphite or acetate ions (see Shapiro, R., DiFate, V., and Welcher, M, (1974) J. Am. Chem. Soc. 96: 906-912).

The incubation with the sulphonating reagent can be carried out at pH below 7 and at a temperature which favors the formation of the uracil sulphonate group. A pH below 7 is optimal for carrying out the sulphonation reaction, which converts the cytosine bases to cytosine sulphonate and subsequently to uracil sulphonate. However, the methods can be performed with the sulphonation reaction above pH 7, if desired.

The sulphonation reaction can be carried out in the presence of an additive capable of enhancing the bisulphite reaction. Examples of suitable additives include, but not limited to, quinol, urea, DTT and methoxyamine. Of these reagents, quinol is a reducing agent. Urea and methyoxyamine are agents added to improve the efficiency of the bisulphite reaction. In addition, DTT can be used in the reaction to prevent the degradation of RNA by endogenous RNases. It will be appreciated that other additives or agents can be provided to assist in the bisulphite reaction. The sulphonation reaction results in methylated cytosines in the nucleic acid sample remaining unchanged while unmethylated cytosines are converted to uracils.

Reaction conditions found to work well are as follows. The DNA, or other nucleic acids, to be treated is made up to a volume of 20 µl and denatured by incubating with 2.2 µl freshly prepared 3 M sodium hydroxide (BDH AnalaR #10252.4X) solution for 15 minutes at 37° C. The concentration of sodium hydroxide and incubation times can be adjusted as necessary to ensure complete denaturation of the template nucleic acid. 220 µl of a freshly prepared solution of 3 M sodium metabisulphite (BDH AnalaR #10356.4D) pH 5.0 (the pH is adjusted by the addition of 10M sodium hydroxide (BDH AnalaR #10252.4X) along with 12 µl of a 100 mM quinol solution (BDH AnalaR #103122E) is added. The concentration of quinol added can be anything in the range of about 10 to 500 mM as determined experimentally. The solution is then vortexed and overlaid with 208 µl of mineral oil (Sigma molecular biology grade M-5904). The sample is then incubated at a suitable temperature and for sufficient time, to allow time for full bisulphite conversion, for example at 80° C. for 45 minutes. It is understood by those skilled in the art that the volumes, concentrations and incubation time and temperature described above can be varied so long as the reaction conditions are suitable for sulphonation of the nucleic acids.

The converted nucleic acids are then desalted either by use of a desalting column, such as Zymo-Spin I columns according to the manufacturer's instructions, or by precipitation. For precipitation, samples are diluted so that the salts inhibitory to subsequent reactions are not co-precipitated with the sulphonated nucleic acids. The salt concentration is diluted to less than about 1 M. Generally, the dilution step is carried out using water or buffer to reduce the salt concentration to below about 0.5M. For example, the salt concentration is generally diluted to less than about 1 mM to about 1 M, in particular, less than about 0.5 M, less than about 0.4 M, less than about 0.3 M, less than about 0.2 M, less than about 0.1 M, less than about 50 mM, less than about 20 mM, less than about 10 mM, or even less than about 1 mM, if desired. One skilled in the art can readily determine a suitable dilution that diminishes salt precipitation with the nucleic acids so that subsequent steps can be performed with minimal further clean up or manipulation of the nucleic acid sample. The dilution is generally carried out in water but can be carried out in any suitable buffer, for example Tris/EDTA or other biological buffers so long as the buffer does not precipitate significantly or cause the salt to precipitate significantly with the nucleic acids so as to inhibit subsequent reactions. Generally, precipitation is carried out using a precipitating agent such as an alcohol. An exemplary alcohol for precipitation of nucleic acids can be selected from isopropanol, ethanol or any other suitable alcohol.

Using enzymes that are capable of processing DNA containing bulky adducts such as sulphonate groups should eliminate the need to de-sulphonate the bisulphite converted nucleic acids. As the desulphonation step is the point at which most nucleic acid damage and loss is seen during the bisulphite conversion method, being able to omit or modify this step, will greatly improve yield and maintain higher molecular weight DNA relative to previously known methods. However, there may be instances where desulphonation of the bisulphite modified nucleic acid is still required, and this can be carried out using standard methods or modified methods as set out below.

The desulphonation step can be carried out by adjusting the pH of the precipitated treated nucleic acid up to about 12.5. Exposure to alkaline environments tends to promote strand breaks in apurinic sites in the DNA induced by the previous exposure to an acidic pH. Therefore, the alkaline pH treatment is minimized if strand breaks are to be avoided. This step can be carried out efficiently at around pH 10.5-11.5 with a suitable buffer or alkali reagent. Examples of suitable buffers or alkali reagents include buffers having a pH 7.0-12.5. It will be appreciated by persons skilled in the art that suitable buffers or alkali reagents can be selected from the vast range of known buffers and alkali reagents available.

Temperature ranges for the desulphonation step are room temperature to about 96° C. and times can vary from 2 minutes to 96 hours or longer depending on the conditions used. One skilled in the art can readily determine a suitable time and temperature for carrying out the desulphonation reaction. Temperatures below room temperature can also be used so long as the incubation time is increased to allow sufficient desulphonation. Thus, the incubation step can be carried out at about 10° C., about 20° C., about 22° C., about 25° C., about 30° C., about 35° C., about 37° C., about 40° C., about 45° C., about 50° C., about 55° C., about 60° C., about 65° C., about 70° C., about 75° C., about 80° C., about 85° C., about 90° C., about 95° C., and about 96° C. A particularly useful temperature for carrying out the desulphonation reaction is in the temperature range of about 75 to 95° C.

The present invention provides methods for characterization of methylated nucleic adds. The methods allow efficient sulphonation (and desulphonation steps if desired) to be carried out on the nucleic acid sample. However, it is understood that neither of the sulphonation or desulphonation steps need be carried out to completion, only sufficiently to subsequently characterize methylation of the nucleic acid, as disclosed herein. One skilled in the art can readily determine whether these steps should be carried out to near completion or whether incomplete reactions are sufficient for a desired analysis. For example, when a small number of cells or a small amount of nucleic acid sample are used, it is generally desired that a more complete reaction be performed. When larger quantities of nucleic acid sample are being characterized, a less complete reaction can be carried out while still providing sufficient reaction products for subsequent analysis of the methylation state of the nucleic acid sample.

The present invention provides methods for the use of enzymes that have enhanced abilities to efficiently process bisulphite modified nucleic acids. These enzymes can be used in the analysis of the methylation state of a genome as a measure of the state of a cell, tissue or organism, as disclosed herein or used to determine the sequence of a given region of nucleic acid. The outcomes of the invention provide several advantages over enzymes currently used for processing methylated nucleic acids. The methods are advantageous in that they will provide a new array of enzymes that will be capable, for example, but not exclusively, of improved PCR amplification efficiency and increased amplicon length of bisulphite modified DNA, and of efficient reverse transcription and/or one-step reverse-transcription PCR of bisulphite modified RNA. The enzymes will have a greater ability to process the abasic sites, sulphonate groups and 3 base genome generated during the bisulphite modification, as well as other nucleic acid damage sites, and also to bypass other bulky adducts, such as, but not limited to, intercalating nucleic acids.

The methods of the present invention may also be used to detect or diagnose microorganisms in accordance with WO 2006/058393 'Methods for simplifying microbial nucleic acids by chemical modification of cytosine' and WO 2096/066353 'Detection of Human Papilloma virus' (Human Genetic Signatures Pty Ltd, Australia), incorporated herein by reference.

The methods of the present invention provide a simplified procedure by which bisulphite modified nucleic acids can be manipulated using common molecular biological techniques, without the need to de-sulphonate the samples, or to de-sulphonate using more gentle methods. As the desulphonation step is the point at which most nucleic acid damage and loss is seen, being able to omit or modify this step, will greatly improve yield and maintain higher molecular weight DNA relative to previously known methods. These enzymes will enable the successful analysis of the methylation state of small numbers of cells, of archival nucleic acids and of large stretches of nucleic acids or whole genes, or be able to measure the presence or absence of small numbers of infectious agents whether DNA or RNA based in clinical samples all of which have been hitherto impossible.

Accordingly, the methods of the present invention provide the additional advantage of allowing even smaller amounts of starting material to be used and efficiently characterized with respect to methylation. The method for determining the methylation state of a sample can be carried out in parallel with a test sample and a control sample so that the methylation state of the sample can be compared and determined relative to a reference sample. For example, the samples can be compared to determine whether there is an increase or decrease of methylation in general or at particular sites. Such a determination can be used to diagnose and/or determine the prognosis of a disease, as discussed herein. The method can further include reporting of the methylation state of a sample, for example, in a diagnostic application.

It is understood that the components for use of the invention can be provided in the form of a kit for efficient processing of bisulphite modified nucleic acids.

Embodiments for utilising engineered enzymes specific for enhanced processing of bisulphite modified nucleic acids are described in non-limiting detail below.

EXAMPLES

Methods and Reagents

Chemicals can be obtained as follows: Ethanol from Aldrich (St. Louis Mo.; 200 proof E702-3); Isopropanol from Sigma (St. Louis Mo.; 99%+Sigma I-9516); Mineral oil from Sigma (M-5904); Quinol from BDH (AnalaR #103122E); Sodium acetate solution 3M from Sigma (5-7899); Sodium chloride from Sigma (ACS reagent S9888); and Sodium hydroxide from BDH (AnalaR #10252.4X); Sodium metabisulphite from BDH (AnalaR #10356); Diethyl ether from Sigma (St. Louis Mo.; 309958): Hexane from Sigma (St. Louis Mo.; 650420); Luria broth from Oxoid (Liverpool; CM0996B); Magnesium chloride from Sigma (St. Louis Mo.; 63069); Mineral oil from Sigma (M-5904); Potassium chloride from Sigma (St. Louis Mo.; 60142); Span 80 From Fluke (Buchs CH; 85548); Tetracycline hydrochloride from Sigma (St. Louis Mo.; T8032); Triton X-100 from Sigma (St. Louis Mo.; 93426); Trizma hydrochloride from Sigma (St. Louis Mo.; T5941); Tween 80 from Sigma (St. Louis Mo.; P8074).

Enzymes/Reagents can be obtained as follows: dNTPs from Promega (Madison Wis.; C1145); Glycogen from Roche (Indianapolis Ind.; #10 901 393 001); tRNA from Roche (Indianapolis Ind.; #10 109 495 001); RNase, DNase-free from Roche (Castle Hill NSW; 11 119 915 001); Sail from New England Biolabs (Beverly Mass.; #R0138L, 20 units/µl); XbaI from New England Biolabs (Beverly Mass.; #R0145L, 20 units/µl); and DNA markers from Sigma (Direct load PCR low ladder 100-1000 bp, Sigma D-3687 and 100-10 Kb, Sigma D-7058); EcoR1 from Roche (Indianapolis Ind.; #87930626, 10 units/µl); HindIII from Biolabs (Beverly Mass.; #R01045, 10 units/µl); PCR master mix from Promega (Madison Wis.; #M7505); and DNA markers from Sigma (Direct load PCR low ladder 100-1000 bp, Sigma D-3687 and 100-10 Kb, Sigma D-7058).

Solutions are as follows: (1) 10 mM Tris/0.1M EDTA, pH 7.0-12.5; (2) 3 M NaOH (6 g in 50 ml water; BDH AnalaR #10252.4X); (3) 3M Metabisulphite (7.6 g in 20 ml water with 416 µl 10 N NaOH (BDH AnalaR #10356.4D); (4) 100 mM Quinol (0.55 g in 50 ml water; BDH AnalaR #103122E); (5) 50×TAE gel electrophoresis buffer (242 g Trizma base, 57.1 ml glacial acetic acid, 37.2 g EDTA and water to 1 l); (6) 5× Agarose gel loading buffer (1 ml 1% Bromophenol blue (Sigma B6131), 1 ml Xylene Cyanol (Sigma X-4126),3.2 ml Glycerol (Sigma G6279), 8 µl 0.6M EDTA pH 8.0, 200 µl 50×TAE buffer and water to 10 ml); and (7) 1×Taq buffer (50 mM KCl, 10 mM Tris-HCl, pH 9.0, 0.1% Triton X-100, 1.5 mM $MgCl_2$).

Bisulphite Treatment of Nucleic Acid

An exemplary protocol for the bisulphite treatment of nucleic acids is set out below and can be used to generate template nucleic acids for amplification or copying by the enzymes according to the present invention. This protocol successfully results in retaining substantially all DNA treated. It will be appreciated that the volumes or amounts of sample or reagents can be varied.

To 2 µg of nucleic acid in a volume of 20 µl, 2.2 µl of 3 M NaOH (6 g in 50 ml water, freshly made) is added. This step denatures the double stranded nucleic acid molecules into a single stranded form, since the bisulphite reagent preferably reacts with single stranded molecules. The mixture is incubated at 37° C. for 15 minutes. Incubation at temperatures above room temperature can be used to improve the efficiency of denaturation.

After the incubation, 220 µl 3M Sodium Metabisulphite (3.35 g in 4.68 ml water with 320 µl 10 N NaOH; BDH AnalaR #10356.4D; freshly made) and 12 µl of 100 mM Quinol (0.55 g in 50 ml water, BDH AnalaR #103122E; freshly made) are added in succession. Quinol is a reducing agent and helps to reduce oxidation of the reagents. Other reducing agents can also be used, for example, dithiothreitol (DTT), mercaptoethanol, quinone (hydroquinone), or other suitable reducing agents. Likewise, additives which enhance the reaction, such as methoxyamine or urea, may also be incorporated. The sample is overlaid with 200 µl of mineral oil which prevents evaporation and oxidation of the reagents, but is not essential. The sample is then incubated for 45 minutes at 80° C. Other temperatures from 25° C. to 90° C. may also be used with incubation lengths varying from 5 minutes to 8 hours, or longer.

After the treatment with sodium metabisulphite, the oil is removed, and 2 µl glycogen (20 mg/ml; Roche #10 901 393 001) or tRNA (Roche #10 109 495 001) are added if the nucleic acid concentration is low. These additives are optional and can be used to improve the yield of nucleic acid obtained by co-precipitating with the target nucleic acid especially when the nucleic acid is present at low concentrations. Typically, glycogen is used in the precipitation of DNA whereas tRNA is used as a coprecipitant with RNA, although other coprecipitants may also be used.

Bisulphite modified nucleic acids are then desalted by use of a desalting spin column such as Zymo-spin columns (Zymo # C1003) according to the manufacturer's instructions. Alternatively, the samples can be isopropanol precipitated as follows: 800 µl of water is added to the sample, mixed and then 1 ml isopropanol is added. The water or buffer reduces the concentration of the bisulphite salt in the reaction vessel to a level at which the salt will not precipitate along with the target nucleic acid of interest. The sample is mixed again and left at 4° C. for 60 minutes, although other temperatures and lengths of incubation can be used as long as it effectively results in precipitation of the nucleic acid. The sample is centrifuged at 15,000×g for 10-15 minutes at 4° C. and the pellet washed with 70% EtOH. This washing treatment removes any residual salts that precipitated with the nucleic acids.

The pellet is allowed to dry and then resuspended in a suitable volume of buffer or water, depending on the downstream application. If desulphonation is desired, resuspension in TE buffer (10 mM Tris, 0.1 mM EDTA) pH 10.5 and incubation at 95° C. for 20 minutes has been found to be particularly effective for desulphonation of DNA samples, Buffers at pH 7.0-12.5 can also be used and the sample may be incubated at 37° C. to 95° C. for 1 min to 96 hr, as needed to facilitate desulphonation of the nucleic acid to a level that is acceptable by the user.

The method described above can be preceded by digestion with one or more restriction enzymes. Two independent restriction enzyme digests are set up of the same sample of DNA as described below. The enzymes selected for digestion are dependent upon the sequence to be amplified. For example, digest 2 µg genomic DNA with EcoRI in a 20 µl volume for 1 hr at 37° C. This step is used to digest the genomic DNA into smaller fragments which are more amenable to bisulphite conversion than genomic DNA. Sonication or physical forces can also be used to shear the DNA into smaller sized fragments. The intensity of sonication and the length of sonication is selected based on the desired size of DNA fragments. A separate digestion reaction is carried out, for example, by digesting 2 µg genomic DNA with HindIII as described above. These or other suitable restriction enzymes can be selected for pretreatment digestion. The digested DNA is treated with metabisulfite as described above.

Generation and Utilization of Enzymes

An example of how to generate a thermostable DNA polymerase for use in amplification of bisulphite converted DNA is given to illustrate the technique and is performed according to the method of d'Abbadie et al (d'Abbadie, M., Hofreiter, M., Vaisman, A., Loakes, D., Gasparutto, D., Cadet, J., Woodgate, R., Paabo, S. and Holliger, P. (2007) Nature Biotech. 25(8), 939-943) with adaptations specific for generating enzymes that are superior in their ability to process bisulphite modified nucleic acid as described below.

DNA polymerase genes Taq and Dpo4 are amplified from *Thermus aquaticus* (Accession no J04639) and *Sulfolobus solfataricus* (Accession no. N002754), respectively, using gene-specific primers with flanking XbaI and SalI restriction sites. Purified PCR products are cloned into pre-digested pASK75 and constructs are transformed into *E. coli* and expressed according to the methods of Ghadessy et al., (Ghadessy, F. J et al., PNAS (1998), 98, (8), 4552-4557) and Skerra (Skerra, A. (1994) Gene, 151, 131-135; which are incorporated herein by reference). For purification, Taq and Dpo4 clones are subcloned with an N-terminal hexahistidine tag introduced via primers, expressed as above, and lysed and purified using Ni-NTA spin columns according to the manufacturer's instructions (Qiagen, #31014).

Molecular breeding is used to yield chimeras of the two enzymes. Briefly, equal concentrations of the two polymerase genes are cycled 40 times (94° C., 30 sec; 55° C., 1 sec) using primers to homologous flanking regions. The short annealing/extension time results in incomplete primer extension during each round. In subsequent cycles, the growing fragments anneal to different templates based on sequence complementarily and extend further, effectively leading to recombination between different genes. The process is continued until full-length sequences are made and more or less cycles may be needed. Fine tuning the extension times gives some control over the length of the gene segments that are swapped and can be altered from the times given here. The products are then gel purified using the QIAquick gel extraction kit according to the manufacturer's instructions (Qiagen, #28706), reamplified and cloned into pASK75 to generate a hybrid polymerase library.

Emulsification and compartmentalised self-replication reactions (CSRs) are then performed as described by d'Abbadie et al (2007) using either matched primers, primers containing abasic sites, desulphonated bisulphite-converted primers or bisulphite-converted primers which have not been desulphonated, or combinations thereof. The CSRs are undertaken by cycling at 94° C. for 5 min, followed by 20 cycles of 94° C. for 1 min, 50° C. for 1 min and 72° C. for 8 min. The initial denaturation for 5 minutes ruptures the bacterial cell harbouring the hybrid polymerase which is then released into the aqueous compartment. This allows the self-replication of the polymerase if the enzyme is active. Non-active enzymes will fail to self-replicate, will not be selected for subsequent rounds and hence will be eliminated from the gene pool.

To recover the reaction mixtures, the emulsions are solvent-extracted and the purified selection products are re-amplified and re-cloned and then screened for their ability to amplify various sized products from bisulphite modified DNA generated as indicated above (either with or without desulphonation) by PCR using 10 pg template DNA, 0.2 mM dNTPs, 1 μM primers in 1×Taq buffer and cycling for 94° C., 5 min, followed by 30 cycles of 94° C., 1 min; 55° C., 1 min; 68-72° C., 30 secs-2 min, depending on the expected product size. Promising clones from selection rounds one and two are StEP shuffled and backcrossed with parent polymerase genes as described above. Recombination, recloning, rescreening and reselection continues until one or more enzymes are generated that have superior ability to amplify bisulphite modified DNA compared to the parent enzymes. In particular, superiority is demonstrated by the ability to generate amplicons more efficiently, in larger quantities, of larger size and/or from non-desulphonated bisulphite-treated DNA than the parent polymerases.

The various mutagenesis and/or recombination techniques available can be used to generate a variety of mutant/chimeric enzymes specifically enhanced for their ability to amplify or copy bisulphite modified nucleic acids including, but not limited to, thermophilic and mesophilic polymerases, reverse transcriptases, and endonucleases. Furthermore, newly discovered enzymes such as the DinB family of polymerases (eg Dpo4 from *Sulfolobus solfataticus*), may exhibit superior ability to amplify bisulphite modified DNA without the need for further mutagenesis or recombination.

FIG. 1 demonstrates the expected results with new polymerases, selected for their ability to process bisulphite converted nucleic acids, in comparison to the parental polymerases. The hybrid/mutant polymerases will exhibit enhanced ability to amplify desulphonated bisulphite modified DNA and be able to amplify larger amplicons compared to parent polymerases and will also be able to amplify from a non-desulphonated template whereas parent polymerases cannot.

Figure 2:
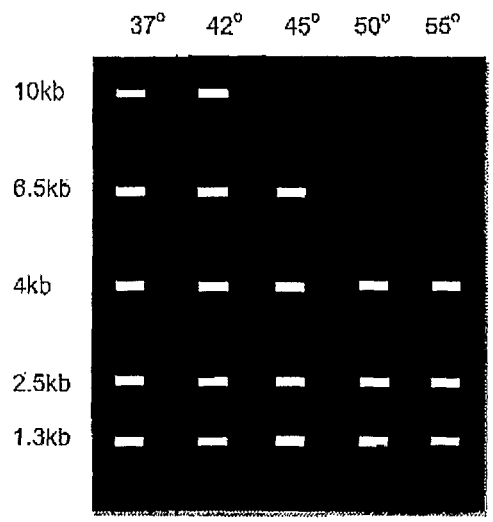
FIG. 2 is a diagram showing expected results of reverse transcription efficiency. $^{32}$P-labelled cDNA was synthesized in 20 µl reactions at the temperatures indicated for 60 minutes, by Superscript III (FIG. 2A and FIG. 2C) and a chimeric reverse transcriptase (B and D), from a mixture of 0.25 µg each of 1.3 kb, 2.5 kb, 4 kb, 6.5 kb and 10 kb total RNA with 200 units of each RT and 0.5 µg random hexamers in Superscript III buffer. The RNA was bisulphite modified and either desulphonated (FIG. 2A and FIG. 2B) or non-desulphonated (C and D). The cDNA products were electrophoresed on a 1.4% alkaline gel and exposed to X-ray film.
Figure 2:
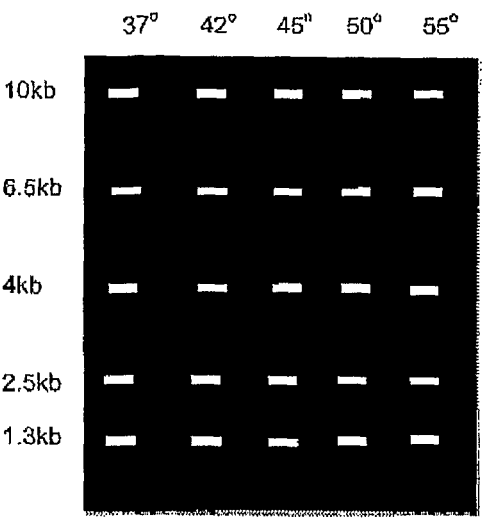
Figure 2:
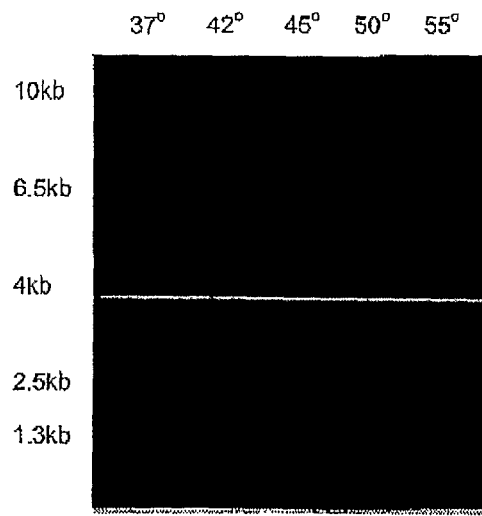
Figure 2:
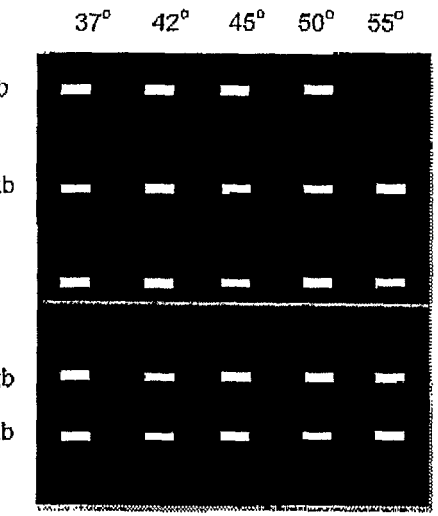

FIG. 2 illustrates the results with new reverse transcriptases, selected for their ability to process converted nucleic acids, in comparison to the parental reverse transcriptases. The new transcriptases will be able to more efficiently copy desulphonated bisulphite converted RNA templates of various sizes compared to available transcriptases, and will also be able to copy from a non-desulphonated template whereas parental reverse transcriptases cannot.

EXPERIMENTAL

HIV-RT Enzyme

HCV RNA was isolated OptiQual® HCV RNA high positive control (Acrometrix cat#96-0203) using the QiAmp UltraSens (Qiagen) viral kit according to the manufacturers instructions and resuspended at a final concentration of 5,000 IU/μl. Bisulphite conversion of RNA.

3.3 g sodium bisulphite (Sigma 59000 500 g; lot number 116K0761) was dissolved in 5 ml Xceed reagent 1. The reagent was heated at 80° C. until fully dissolved, allow to cool.

0.11 g of Hydroquinone (Merck 8.22333.0250; lot number K36100033 702) was dissolved in 10 ml nuclease-free water.

5 μl of RNA was mixed with 220 μl bisulphite reagent and 12 μl quinol in a PCR tube and incubated at 70° C. for 20 minutes in a PCR machine.

800 μl nuclease-free water was added along with 2 μl glycoblue (Ambion AM9515; lot number 0705003), the samples mixed well, then 1 ml isopropanol was added and the samples incubated at 4° C. for 1 hour.

The RNA was pelleted by centrifuging at 16 000×g for 20 minutes at 4° C.

The supernatant discarded and the pellet washed with 1 ml 70% ethanol with moderate vortexing. The sample was recentrifuge at 16 000×g for 7 minutes at 4° C.

The supernatant was discarded and the pellet air dried for a few minutes.

The pellet was resuspended pellet in 70 μl desulphonation buffer (Xceed reagent 5) and de-sulphonate at 76° C. for 0-15 minutes in a PCR machine.

The RNA was cooled, then 8 μl of a mastermix added comprising the following per reaction;

10 μl converted RNA

1 μl 10 mM dNTPS

1 μl random H primers (300 ng/μl)

The sample was heated at 65° C. far 5 minutes, then placed on ice for at least 1 minute. Add 7 μl of a mastermix comprising the following per reaction:

| HIV-RT | Control RT |
|---|---|
| 2 μl 10× HIV-RT Buffer | 4 μl 5× FS buffer |
| 1 μl HIV-RT (1 U/μl) | 1 μl 0.1M DTT |
| 1 μl Rnase OUT | 1 μl Superscript III |
| 4 μl water | 1 μl Rnase OUT |

The samples were mixed the reverse transcription carried out as follows; 25° C. for 2 mins, 27° C. for 2 mins, 29° C. for 2 mins, 31° C. for 2 mins, 33° C. for 2 mins, 35° C. for 2 mins, 37° C. for 30 mins, 45° C. for 10 mins, 50° C. for 10 mins, 70° C. for 5 mins, then soaked at 15° C.

Take 5 μl of the cDNA for analysis by PCR, comprising the following per reaction;

36.5 μl Promega mastermix 1.0 μl F1 primer (100 ng/μl)

1 μl R0 primer (100 ng/μl)

6.5 μl water

Note: primers are labelled RNA primers in orange box in "Herbert"

Cycling conditions are as follows:

95° C., 3 mins

95° C., 10 secs

52° C., 1 min 40×

68° C., 1 min

68° C., 7 mins

Figure 3:
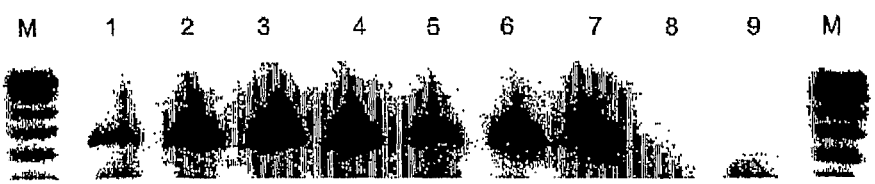
FIG. 3 shows results of amplification of bisulphite treated RNA using HIV-RT reverse transcriptase. Lane 1. 0 minutes desulphonation @ 76° C.; Lane 2. 1 minutes desulphonation @ 76° C.; Lane 3. 2 minutes desulphonation @ 76° C.; Lane 4. 5 minutes desulphonation @ 76° C.; Lane 5. 10 minutes desulphonation @ 76° C.; Lane 6. 15 minutes desulphonation @ 76° C.; Lane 7. 15 minutes desulphonation @ 76° C. (control reverse transcriptase); Lane 8. RT negative control; Lane 9. PCR negative control.

As can be seen from FIG. 3 the HIV-RT was able to copy bisulphite treated RNA without the additional desulphonation step.

5D4 Enzyme
Bisulphite Conversion Reactions

1 μg of template material was made to a final volume of 20 μl. The template was denatured by the addition of 2 μl of 3M NaOH for 15 minutes at 37° C. The DNA was then bisulphite treated according to the MethylEasy Xceed bisulphite conversion kit (Human Genetic Signatures, Sydney, Australia). For desulphonation, the converted DNA was heated at 80° C. for 20 minutes then stored at −20° C. until required. Non-desulphonated bisulphite treated DNA was resuspended in water (instead of reagent #5 from the MethylEasy kit) and used immediately.

Primer Extension Reactions

Reactions were prepared in 50 μl volumes containing 2 μl of 100 μM template oligonucleotide, 2 μl of 2.5 μM Cy3 labelled oligonucleotide, 5 μl of polymerase buffer, 4 μl dNTPs (625 μM each gives a final concentration of 50 μM) and distilled water to 49 μl.

```
BStemp3
                                       (SEQ ID NO: 1)
5'-TAGCACCCTAGCCAGCTAGCTGGGTATAGTGAGTGGTATTA BStempC8
                                       (SEQ ID NO: 2)
5'-CCCCCCCCTGGGTATAGTGAGTGGTATTA Primer
                                       (SEQ ID NO: 3)
5'-7C6C5CTATACCCA 7 = Cy3
6 = LNA T
6 = LNA A
(CTCACTATACCC (SEQ ID NO: 4))
```

Samples were heated to 85° C. for 2 minutes then cooled slowly to 40° C. for 1 minute. The samples were then heated to 55° C. for a further 1 minute then 1 μl of a 1/10 dilution of each enzyme added and the samples incubated for the appropriate time. The reaction was stopped by the addition of 50 μl of 8M Urea, 50 mM EDTA.

The samples were then heated to 95° C. for 2 minutes then snap chilled on ice. 10 μl of the sample was run on a 20% denaturing acrylamide gel at 30 W for 3 hours. Fluorescence was then recorded on a Typoon imager.

PCR Amplification

Amplification reactions were prepared in a final reaction volume of 25 μl containing 2.5 μl of X10 SuperTaq buffet, 1 μl of 10 mM dNTP's, 1 μl of 100 ng/μl each primer, 0.5 μl SuperTaq (Cambia Ltd, Cambridge, United Kingdom) and 18 μl of distilled water, 1 μl of template was added.

Primers

```
F1    5'-GAGGTTTGGAAGTTTTATTTTATT    (SEQ ID NO: 5)

R1    5'-TAACTTATCATCAAAATAAAC       (SEQ ID NO: 6)

R3    5'-TATACTACCTCAAAAATATAAATA    (SEQ ID NO: 7)

R5    5'-AAAAATCCTTACAAAACTTATAAG    (SEQ ID NO: 8)
```

Template plasmid Tgo was kindly provided by Vitor Pinheiro (MRC laboratory for

Amplification was carried out on a MJ Research PTC-200 (PTC200) DNA Engine Thermal Cycler PCR using the following PCR program 94° C. 1 min 30 seconds
94° C. 20 seconds
45° C. 30 seconds Repeated X24
68° C. 1 minute PCR products were resolved on a 1.5% agarose gel containing ethidium bromide.

Table 1 shows the results of a primer extension reaction using 6 different polymerase enzymes using a partially desulphonated BStemp3 template. As can be seen from Table 1 the only enzymes that partially copy full length sulphonated (S) bisulphite treated template are the Taq polymerase, 5D4 and 3A10 enzymes. Enzymes 14, 5D4, 3A10, E10 and Tgo were all generated by Compartmentalised Self Replication (CSR) and defined in EP 18012113 (Medical Research Council). 5D4 was thus chosen for further characterisation.

TABLE 1

Primer extension analysis of various mutant polymerases using desulphonated and sulphonated bisulphite treated template.

|         | Taq | 14  | 5D4 | 3A10 | E10 | Tgo-L | Tgo-P |
|---------|-----|-----|-----|------|-----|-------|-------|
| Control | Yes | Yes | Yes | Yes  | Yes | Yes   | Yes   |
| Desulph | Yes | Yes | Yes | Yes  | No  | No    | No    |
| Sulph   | Yes | No  | Yes | Yes  | No  | No    | No    |

Tgo-L = crude lysate
Tgo-P = purified enzyme.

Table 2 shows a time course primer extension experiment using Control (C), Desulphonated (D) and Sulphonated (S) bisulphite treated BStemp3 template. The results show that even after as little as 1 minute the modified 5D4 enzyme is able to produce full-length product from the sulphonated template. After 15 minutes the 5D4 has copied the sulphonated template to completion while the wild type Taq polymerase still shows multiple stops indicating that the enzyme does not process sulphonated templates efficiently. Interestingly, 5D4 also seems to copy desulphonated material more efficiently that the Taq polymerase.

TABLE 2

Time course primer extension using Taq polymerase and 5D4 with desulphonated and sulphonated bisulphite treated templates.

| | Full length product generated | | | | | |
|---|---|---|---|---|---|---|
| | Taq Polymerase | | | 5D4 | | |
| | 1 min | 5 min | 15 min | 1 min | 5 min | 15 min |
| Control  | +++ | +++ | +++ | +++ | +++ | +++ |
| Desulpho | +   | ++  | +++ | ++  | +++ | +++ |
| Sulphon  | −   | +   | ++  | +   | ++  | +++ |

− No full length product generated
+ Low levels of full length product
++ Considerable full length product.
+++ All product full length product.

Table 3 shows the results of a 5 minute primer extension reaction carried out on a C8 template. Again the 5D4 enzyme can be seen to be superior to the Taq polymerase with regard to its ability to copy both desulphonated and sulphonated targets containing a run of C's. Indeed the 5D4 completely copies the template while the wild type Taq polymerase again produces multiple stops.

TABLE 3

Comparison of 5D4 and Taq polymerase using a poly C8 bisulphite treated desulphonated and sulphonated templates.

|  | Taq Polymerase | | | 5D4 | | |
| --- | --- | --- | --- | --- | --- | --- |
|  | Control | Desulph | Sulphon | Control | Desulph | Sulphon |
| C#1 | − | + | + | − | − | − |
| C#2 | − | + | + | − | − | − |
| C#3 | − | ++ | + | − | + | +/− |
| C#4 | − | ++ | ++ | − | + | +/− |
| C#5 | − | ++ | ++ | − | + | +/− |
| C#6 | − | + | ++ | − | + | +/− |
| C#7 | − | ++ | +++ | − | + | +/− |
| C#8 | − | + | ++ | − | +/− | +/− |

− Indicates no bocks observed on the gel.
+/− Indicates very faint stops observed.
+ Multiple blockage products.
++ Multiple heavy blockages.
+++ Intense stoppage products.

Table 4 shows both the fidelity of the 5D4 and again the superior ability to bypass sulphonated DNA lesions compared to Taq polymerase which is blocked by the sulphonated C templates.

NB after bisulphite treatment, C residues are converted to U, which are then copied by the polymerase as a T thus the polymerase should only add A into the growing chain if the enzyme exhibits 100% fidelity.

TABLE 4

Fidelity and processivity of 5D4 and Taq polymerase using a poly C8 bisulphite treated desulphonated and sulphonated templates.

|  | Taq Polymerase | | | 5D4 | | |
| --- | --- | --- | --- | --- | --- | --- |
|  | Control | Desulph | Sulphon | Control | Desulph | Sulphon |
| G | Yes | No | No | Yes | No | No |
| A | No | Yes | Blocked | No | Yes | Yes |
| T | No | No | No | No | No | No |
| C | No | No | No | No | No | No |

Figure 4:
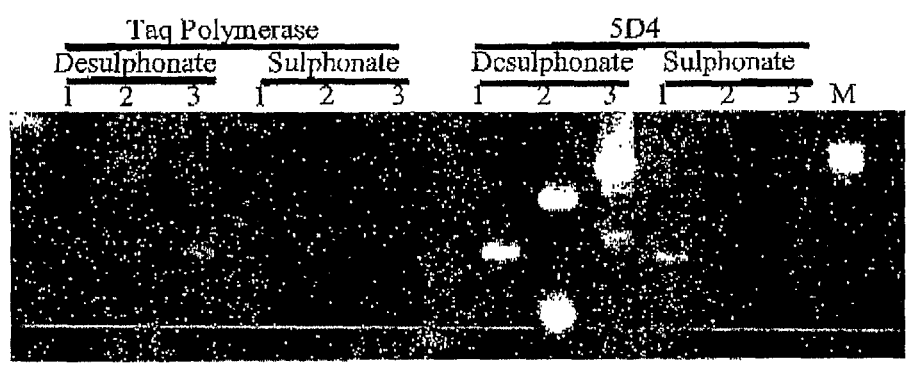
FIG. 4 shows comparison of PCR amplification efficiency between Taq and 5D4 enzymes.

A comparison between Taq polymerase and 5D4 in a PCR reaction was carried out and the results are shown in FIG. 4. Conditions were as follows:
Template: Tgo plasmid bisulphite treated
Primers: Set 1 amplify 250 bp fragment
   Set 2 amplify 600 bp fragment
   Set 3 amplify 1050 bp fragment
94° C.—20 seconds
45° C.—30 seconds; 25 cycles
63° C.—1 minute FIG. 4 shows the improved amplification achieved by 5D4 in a standard PCR reaction using bisulphite treated DNA. The enzyme is also able to copy a 250 bp sulphonated template as can be seen from the arrow.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for copying or amplifying bisulphite treated nucleic acid comprising:
   bisulphite treating a nucleic acid; and
   copying or amplifying the bisulphite treated nucleic acid using enzyme Pol A DNA polymerase variant 5D4 (5D4) wherein 5D4 copies or amplifies bisulfite modified nucleic acid more effectively with less or no errors compared to Taq polymerase.

2. The method according to claim 1 wherein the bisulphite treatment uses sodium bisulphite or sodium metabisulphite.

3. The method according to claim 1 wherein the bisulphite treatment is substantially without a desulphonation step.

4. The method according to claim 1 further comprising denaturing the nucleic acid prior to bisulphite treatment.

5. The method according to claim 4 wherein the denaturing step is carried out by providing an alkali environment or by heating the nucleic acid.

6. The method according to claim 1 wherein any methylated nucleotides in the sample remain unchanged while unmethylated nucleotides are converted to uracil by the bisulphite treatment.

7. The method according to claim 1 further comprising desalting or isolating the treated nucleic acid sample.

8. The method according to claim 1 further comprising processing or analysing the treated nucleic acid to determine nucleotide sequence, methylation status, identify a source of nucleic acid, or detect a microorganism.

9. The method according to claim 1 wherein the amplification of the bisulphite treated nucleic acid is carried out by polymerase chain reaction (PCR), Reverse-Transcriptase PCR, qPCR, isothermal amplification, or signal amplification.

10. The method according to claim 1 wherein the treated nucleic acid comprises bisulphite modified DNA, bisulphite modified RNA, or a combination of bisulphite modified DNA and bisulphite modified RNA.

11. The method according to any claim 1 wherein the enzyme is capable of copying or amplifying nucleic acid having abasic sites, bulky adducts including sulphonate groups, having substantially only A, T, G and U bases, or substantially only having A, T and G bases.

\* \* \* \* \*

SEQUENCE LISTING

```
<160> NUMBER OF SEQ ID NOS: 8

<210> SEQ ID NO 1
<211> LENGTH: 41
<212> TYPE: DNA
<213> ORGANISM: Artificial Sequence
<220> FEATURE:
<223> OTHER INFORMATION: Oligonucleotide primer

<400> SEQUENCE: 1
tagcacccta gccagctagc tgggtatagt gagtggtatt a                          41

<210> SEQ ID NO 2
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 2
cccccccctg ggtatagtga gtggtatta                                        29

<210> SEQ ID NO 3
<211> LENGTH: 11
<212> TYPE: DNA
<213> ORGANISM: Artificial Sequence
<220> FEATURE:
<223> OTHER INFORMATION: Oligonucleotide primer

<400> SEQUENCE: 3
ccctataccc a                                                           11
```

```
<210> SEQ ID NO 4
<211> LENGTH: 13
<212> TYPE: DNA
<213> ORGANISM: Artificial Sequence
<220> FEATURE:
<223> OTHER INFORMATION: Oligonucleotide primer

<400> SEQUENCE: 4
ctcactatac cca                                                          13

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 5
gaggtttgga agttttattt tatt                                              24

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 6
taacttatca tcaaaataaa c                                                 21

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 7
tatactacct caaaaatata aata                                              24

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 8
aaaaatcctt acaaaactta taac                                              24
```